(12) United States Patent
Bennett et al.

(10) Patent No.: US 9,732,111 B2
(45) Date of Patent: Aug. 15, 2017

(54) 2'-ALKYNYL SUBSTITUTED NUCLEOSIDE DERIVATIVES AND METHODS OF USE THEREOF FOR THE TREATMENT OF VIRAL DISEASES

(71) Applicant: Merck Sharp & Dohme Corp., Rahway, NJ (US)

(72) Inventors: Frank Bennett, Cranford, NJ (US); Yuhua Huang, Westfield, NJ (US); Lingyan Wang, East Brunswick, NJ (US); Stephane L. Bogen, Somerset, NJ (US); Angela D. Kerekes, Plainfield, NJ (US); Vinay M. Girijavallabhan, Whippany, NJ (US); Gabor Butora, Martinsville, NJ (US); Quang Truong, Morganville, NJ (US); Ian Davies, Princeton, NJ (US); Ann E. Weber, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/443,922

(22) PCT Filed: Nov. 14, 2013

(86) PCT No.: PCT/US2013/069965
§ 371 (c)(1),
(2) Date: May 19, 2015

(87) PCT Pub. No.: WO2014/078463
PCT Pub. Date: May 22, 2014

(65) Prior Publication Data
US 2015/0299243 A1 Oct. 22, 2015

Related U.S. Application Data

(60) Provisional application No. 61/728,045, filed on Nov. 19, 2012.

(51) Int. Cl.

| | | |
|---|---|---|
| *A01N 43/04* | (2006.01) |
| *A61K 31/70* | (2006.01) |
| *C07H 19/10* | (2006.01) |
| *A61K 45/06* | (2006.01) |
| *A61K 31/7072* | (2006.01) |
| *C07H 19/06* | (2006.01) |
| *C07H 19/067* | (2006.01) |
| *C07H 19/09* | (2006.01) |
| *C07H 19/11* | (2006.01) |
| *A61K 31/706* | (2006.01) |
| *A61K 31/7064* | (2006.01) |
| *A61K 31/7068* | (2006.01) |

(52) U.S. Cl.
CPC ......... *C07H 19/10* (2013.01); *A61K 31/7072* (2013.01); *A61K 45/06* (2013.01); *C07H 19/06* (2013.01); *C07H 19/067* (2013.01); *C07H 19/09* (2013.01); *C07H 19/11* (2013.01); *A61K 31/706* (2013.01); *A61K 31/7064* (2013.01); *A61K 31/7068* (2013.01)

(58) Field of Classification Search
None
See application file for complete search history.

(56) References Cited

U.S. PATENT DOCUMENTS

| | | | |
|---|---|---|---|
| 7,629,328 B2 | 12/2009 | Roberts et al. | |
| 7,879,815 B2 | 2/2011 | MacCoss et al. | |
| 2004/0110718 A1* | 6/2004 | Devos .................... | C07H 19/16 514/45 |
| 2007/0275912 A1 | 11/2007 | Bhat et al. | |
| 2009/0318380 A1 | 12/2009 | Sofia et al. | |
| 2010/0081628 A1 | 4/2010 | Du et al. | |

FOREIGN PATENT DOCUMENTS

| | | |
|---|---|---|
| WO | WO2005003147 | 1/2005 |
| WO | WO2008005542 | 1/2008 |
| WO | WO2005030258 | 4/2008 |
| WO | WO2008082484 | 7/2008 |

(Continued)

OTHER PUBLICATIONS

Buff et al. Bioorganic Medicinal Chemistry Letters (1998), vol. 8, pp. 521-524.*
Hayakawa et al. Chem. Pharm. Bull. (1987), vol. 35, pp. 2605-2608.*
Ross et al. JOC (2011), vol. 76, pp. 8311-8319.*
Gao et al. Nature (2010), vol. 465, pp. 96-102.*

(Continued)

*Primary Examiner* — Patrick Lewis
(74) *Attorney, Agent, or Firm* — Jeffrey D. Bergman; Catherine D. Fitch

(57) ABSTRACT

The present invention relates to 2'-Alkynyl Substituted Nucleoside Derivatives of Formula (I): and pharmaceutically acceptable salts thereof, wherein B, X, R1, R2, R3 and R4 are as defined herein. The present invention also relates to compositions comprising at least one 2'-Alkynyl Substituted Nucleoside Derivative, and methods of using the 2'-Alkynyl Substituted Nucleoside Derivatives for treating or preventing HCV infection in a patient.

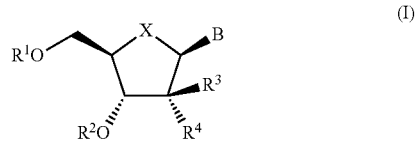

(I)

17 Claims, No Drawings

(56) References Cited

FOREIGN PATENT DOCUMENTS

| WO | WO2008082488 | 7/2008 | |
|----|----|----|----|
| WO | WO2008082601 | 7/2008 | |
| WO | WO2008082602 | 7/2008 | |
| WO | WO2008083351 | 7/2008 | |
| WO | WO2008136815 | 11/2008 | |
| WO | WO2009032116 | 3/2009 | |
| WO | WO2009032123 | 3/2009 | |
| WO | WO2009032124 | 3/2009 | |
| WO | WO2009032125 | 3/2009 | |
| WO | WO2009132123 | 10/2009 | |
| WO | WO2010002877 | 1/2010 | |
| WO | WO2010075517 | 7/2010 | |
| WO | WO2010075549 | 7/2010 | |
| WO | WO2011035231 | 3/2011 | |
| WO | WO2012012465 A1 | 1/2012 | |
| WO | WO 2012/142085 A1 * | 10/2012 | ............ A61K 31/70 |

OTHER PUBLICATIONS

Asselah, et al., "Protease and Polymerase Inhibitors for the Treatment of Hepatitis C", Liver International, 2009, 57-67, 29(s1).

Balsano, "Recent Advances in Antiviral Agents: Established and Innovative Therapies for Viral Hepatitis," Mini-Reviews in Medicinal Chemistry, 2008, pp. 307-318, 8(4).

Beaulieu, et al., "Inhibitors of the HCV NS5B Polymerase: New Hope for the Treatment of Hepatitis C Infections", Current Opinions in Investigational Drugs, 2004, 838, 5.

Berge, et al., "Pharmaceutical Salts", J. Pharm Sci., 1977, pp. 1-19, 66.

Bingham, et al., "Over One Hundred Solvates of Sulfathiazole", Chem. Commun., 2001, 603-604.

Bobeck, et al., "Advances in Nucleoside Monophosphate Prodrugs as Anti-HCV Agents", Antiviral Therapy, 2010, 935-950, 15.

Caira ,et al., "Preparation and Crystal Characterization of a Polymorph,a Monohydrate, and an Ethyl Acetate Solvate of the Antifungal Fluconazole", J. Pharmaceutical Sci, 2004, 601-611, 93(3).

Chatel-Chaix, et al., "Direct-acting and Host-Targeting HCV Inhibitors: Current and Future Directions", Current Opinion in Virology, 2012, 588-598, 2.

Dore, et al., "The Changing Therapeutic Landscape for Hepatitis C", Med. J. Australia, 2012, 629-632, 196.

Eldrup, et al., "Structure-Activity Relationship of Purine Ribonucleosides for Inhibition of Hepatitis C Virus RNA-Dependent RNA Polymerase", J. Med. Chem., 2004, 2283-2295, 47.

Elsa C. Van Tonder, et al, "Preparation and Physicochemical Characterization of 5 Niclosamide Solvates and 1 Hemisolvate", AAPS Pharmscitech, 2004, pp. 1-10, 5(1), US.

Gould, "Salt Selection for basic Drugs", International J. of Pharmaceutics, 1986, 201-217, 33.

Holland, et al., "Hepatitis C Genotyping by Direct Sequencing of the Product rom the Roche Amplicor Test: Methodology and Application to a South Australian Population", Pathology, 1998, 192-195, 30.

Ishii, et al., "Expression of Hepatitis C Virus NS5B Protein: Characterization of Its RNA Polymerase Activity and RNA Binding", Hepatology, 1999, 1227-1235, 29.

Lieven J. Stuyver, et al, "Antiviral Activities and Cellular Toxicities of Modified 2',3'-Dideoxy-2', 3'-Didehydrocytidine Analogs", Antimicrobial Agents and Chemotherapy, 2002, pp. 3854-3860, vol. 46, No. 12, US.

Lohmann, et al., "Biochemical and Kinetic Analyses of NS5B RNA-Dependent RNA Polymerase of the Hepatitis C Virus", Virology, 1998, 108-118, 249.

Ni et al., "Progress and Development of Small Molecule HCV Antivirals", Current Opinion in Drug Discovery and Development, 2004, 446, 7(4).

Poorad et al., "Treating hepatitis C: Current Standard of Care and Emerging Direct-acting Antiviral Agents", Journal of Viral Hepatitis, 2012, 449-464, 19.

Simmonds et al., "Classification of Hepatitis C Virus Into Six Major Genotypes and a Series", J. Gen Virol, 1993, 2391-2399, 74(Pt11).

T. Higuchi and V. Stella, Pro-drugs as NovelDelivery Systems (1987) 14 of the A.C.S. Symposium Series.

Tan et al., "Hepatitits C Therapeutics: Current Status and Emerging Strategies", Nature Review, 2002, 867-881, 1.

Harry-O'kuru, et al, "A Short, Flexible Route Toward 2'-C-Branched Ribonucleosides", J. Org. Chem, 1997, pp. 1754-1756, vol. 62.

Harry-O'kuru, et al, "2'-C-Alkylribonucleosides: Design, Synthesis, and Conformation", Nucleosides & Nucleotides, 1997, pp. 1457-1460, 16(7-9).

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 1
cacccaagaa cagggtttgt                                                    20

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 2
tggccatggg tatgttgtta a                                                  21

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 3
ttaccgggct ctgccatct                                                     19

<210> SEQ ID NO 4
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 4
tgcccgccat catccta                                                       17

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 5
```

```
cgtctgttat gtaaaggatg cgt                                          23

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 6
tcctcatcgc cctcccatcc c                                            21
```

2'-ALKYNYL SUBSTITUTED NUCLEOSIDE DERIVATIVES AND METHODS OF USE THEREOF FOR THE TREATMENT OF VIRAL DISEASES

CROSS-REFERENCE TO RELATED APPLICATIONS

This application is the national stage application under 35 U.S.C. 371 of International Patent Application No. PCT/US2013/069965, filed Nov. 14, 2013, which claims priority to U.S. Provisional Application No. 61/728,045, filed Nov. 19, 2012. Each of the aforementioned PCT and priority applications is incorporated by reference in its entirety.

REFERENCE TO SEQUENCE LISTING SUBMITTED ELECTRONICALLY

The sequence listing of the present application is being submitted electronically via EFS-Web as an ASCII formatted sequence listing with a file name "23365USPCT-SEQTXT-2015MAY19.txt", creation date of May 19, 2015 and a size of 2 KB. This sequence listing submitted via EFS-Web is part of the specification and is herein incorporated by reference in its entirety.

FIELD OF THE INVENTION

The present invention relates to 2'-Alkynyl Substituted Nucleoside Derivatives, compositions comprising at least one 2'-Alkynyl Substituted Nucleoside Derivative, and methods of using the 2'-Alkynyl Substituted Nucleoside Derivatives for treating or preventing HCV infection in a patient.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are over 3 million chronically infected people in the United States alone, according to the U.S. Center for Disease Control. About 150 million individuals are chronically infected worldwide, with at least 3 to 4 million people being infected each year. Hepatitis C Fact Sheet, World Health Organization, July 2012. Once infected, about 20% of people clear the virus, but the rest harbor HCV the rest of their lives. Ten to twenty percent of chronically infected individuals eventually develop liver-destroying cirrhosis or cancer. HCV is transmitted parenterally by contaminated blood and blood products, contaminated needles, or sexually and vertically from infected mothers or carrier mothers to their off-spring.

Different approaches to HCV therapy have been taken, which include the inhibition of viral serine proteinase (NS3 protease), helicase, and RNA-dependent RNA polymerase (NS5B), and the development of a vaccine. Current and investigational treatments for HCV infection are reviewed in Poordad et al., Treating hepatitis C: current standard of care and emerging direct-acting antiviral agents. *Journal of Viral Hepatitis* 19: 449-464 (2012); Asselah et al., Protease and polymerase inhibitors for the treatment of hepatitis C. *Liver International* 29(s1): 57-67 (2009); G. J. Dore. The changing therapeutic landscape for hepatitis C. *Med. J. Australia* 196: 629-632 (2012); and Balsano, *Mini Rev. Med. Chem.* 8(4): 307-318, 2008. Despite the availability of therapeutic treatment options, chronic HCV infection remains a major healthcare concern. Moreover, there is no established vaccine for HCV. Consequently, there is a need for improved therapeutic agents that effectively combat chronic HCV infection.

The HCV virion is an enveloped positive-strand RNA virus with a single oligoribonucleotide genomic sequence of about 9400 bases which encodes a polyprotein of about 3,000 amino acids. The protein products of the HCV gene consist of the structural proteins C, E1, and E2, and the non-structural proteins NS2, NS3, NS4A, NS4B, and NS5B. The nonstructural (NS) proteins are believed to provide the catalytic machinery for viral replication.

The NS3 protease releases NS5B, the RNA-dependent RNA polymerase from the polyprotein chain. HCV NS5B polymerase is required for the synthesis of a negative-strand RNA intermediate from a positive-strand genomic viral RNA that serves as a template in the replication cycle of HCV. NS5B polymerase is an essential component in the HCV replication complex. See K. Ishi, et al., "Expression of Hepatitis C Virus NS5B Protein: Characterization of Its RNA Polymerase Activity and RNA Binding," *Hepatology*, 29:1227-1235 (1999) and V. Lohmann, et al., "Biochemical and Kinetic Analyses of NS5B RNA-Dependent RNA Polymerase of the Hepatitis C Virus," *Virology*, 249: 108-118 (1998). Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in Poordad et al. (2012), supra; Asselah et al. (2009), supra; and Chatel-Chaix et al. Direct-acting and host-targeting HCV inhibitors: current and future directions. *Current Opinion in Virology*, 2:588-598 (2012). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.*, 47:2283-2295 (2004). Nucleoside analogs said to be useful in the treatment of hepatitis C are disclosed in WO 2011/035231, WO 2005/003147, WO 2010/0081628, U.S. Pat. No. 7,879,815, WO 2010/075517, WO 2010/002877, and WO 2009/132123.

SUMMARY OF THE INVENTION

In one aspect, the present invention provides Compounds of Formula (I):

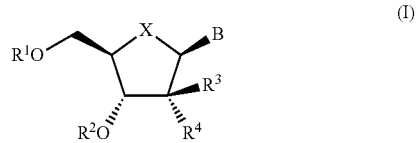

or a pharmaceutically acceptable salt thereof,
wherein:
  B is a pyrimidine base;
  X is O, S or $CH_2$;

$R^1$ is H,

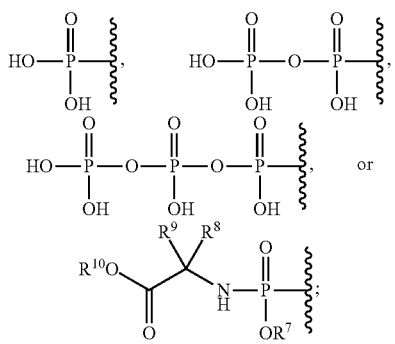

$R^2$ is H, —C(O)—($C_1$-$C_6$ alkyl) or

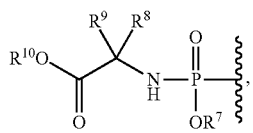

or $R^1$ and $R^2$ join to form a group having the formula:

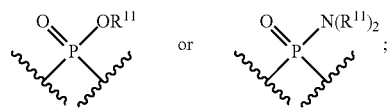

$R^3$ is H, F, —$OR^{12}$, $NH_2$, —CN, $N_3$, —$SR^{12}$ or —C≡$CR^5$;

$R^4$ is H, F, —$OR^{12}$, $NH_2$, —CN, $N_3$, —$SR^{12}$, —O—($C_6$-$C_{10}$ aryl) or —C≡$CR^5$, such that at least one of $R^3$ and $R^4$ is —C≡$CR^5$;

$R^5$ is H, $C_1$-$C_6$ alkyl, ethynyl, $C_3$-$C_7$ cycloalkyl, —$C_6$-$C_{10}$ aryl, wherein said $C_1$-$C_6$ alkyl group, said ethynyl group, said $C_3$-$C_7$ cycloalkyl group and said —$C_6$-$C_{10}$ aryl group can be optionally substituted with one or more $R^6$ groups;

each occurrence of $R^6$ is independently selected from $C_1$-$C_6$ alkyl, halo, —$OR^{12}$, $N(R^{12})_2$, —CN, $C_3$-$C_7$ cycloalkyl, phenyl and benzyl;

$R^7$ is H, $C_6$-$C_{10}$ aryl, 5- or 6-membered monocyclic heteroaryl, 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with halo, $C_1$-$C_6$ alkyl, —O—($C_1$-$C_6$ alkyl) or —($C_1$-$C_3$ alkylene)-C(O)O—($C_1$-$C_6$ alkyl);

$R^8$ is H, $C_1$-$C_6$ alkyl, $C_3$-$C_7$ cycloalkyl, phenyl or benzyl;

$R^9$ is H, $C_1$-$C_6$ alkyl, $C_3$-$C_7$ cycloalkyl, phenyl or benzyl;

$R^{10}$ is H, $C_1$-$C_{20}$ alkyl, $C_2$-$C_{20}$ alkenyl, —($C_1$-$C_3$ alkylene)$_m$-($C_3$-$C_7$ cycloalkyl) or —($C_1$-$C_3$ alkylene)$_m$-($C_6$-$C_{10}$ aryl);

$R^{11}$ is H, $C_1$-$C_6$ alkyl, $C_3$-$C_7$ cycloalkyl, —($C_1$-$C_3$ alkylene)$_m$-$C_6$-$C_{10}$ aryl, 5- or 6-membered monocyclic heteroaryl, 9- or 10-membered bicyclic heteroaryl;

each occurrence of $R^{12}$ is independently H, $C_1$-$C_6$ alkyl, $C_3$-$C_7$ cycloalkyl or $C_6$-$C_{10}$ aryl; and each occurrence of m is independently 0 or 1.

The Compounds of Formula (I) (also referred to herein as the "2'-Alkynyl Substituted Nucleoside Derivatives") and pharmaceutically acceptable salts thereof can be useful, for example, for inhibiting HCV viral replication or replicon activity, for inhibiting HCV NS5B activity, and for treating or preventing HCV infection in a patient. Without being bound by any specific theory, it is believed that the 2'-Alkynyl Substituted Nucleoside Derivatives inhibit HCV viral replication by inhibiting HCV NS5B.

Accordingly, the present invention provides methods for treating or preventing HCV infection in a patient, comprising administering to the patient an effective amount of at least one 2'-Alkynyl Substituted Nucleoside Derivative.

The details of the invention are set forth in the accompanying detailed description set forth below.

Other embodiments, aspects and features of the present invention are either further described in or will be apparent from the ensuing description, examples and appended claims.

DETAILED DESCRIPTION OF THE INVENTION

The present invention relates to 2'-Alkynyl Substituted Nucleoside Derivatives, compositions comprising at least one 2'-Alkynyl Substituted Nucleoside Derivative, and methods of using the 2'-Alkynyl Substituted Nucleoside Derivatives for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of 2'-Alkynyl Substituted Nucleoside Derivative and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood or severity of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —$NH_2$(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

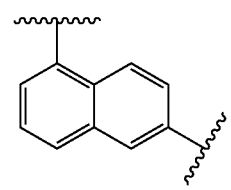

is understood to represent both:

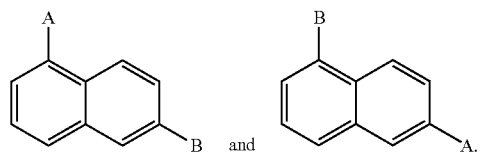

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

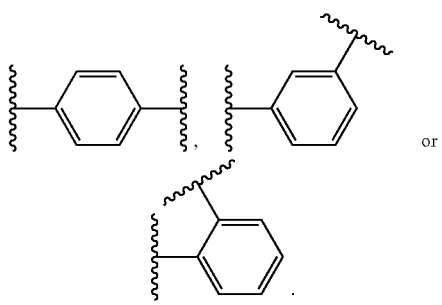

Unless otherwise indicated, an arylene group is unsubstituted.

The term "cycloalkyl," as used herein, refers to a non-aromatic mono- or multicyclic ring system comprising from 3 to about 10 ring carbon atoms. In one embodiment, a cycloalkyl contains from about 5 to about 10 ring carbon atoms. In another embodiment, a cycloalkyl contains from 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

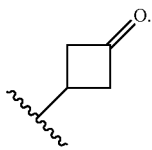

The term "halo," as used herein, means —F, —Cl, —Br or —I.

The term "haloalkyl," as used herein, refers to an alkyl group as defined above, wherein one or more of the alkyl group's hydrogen atoms have been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

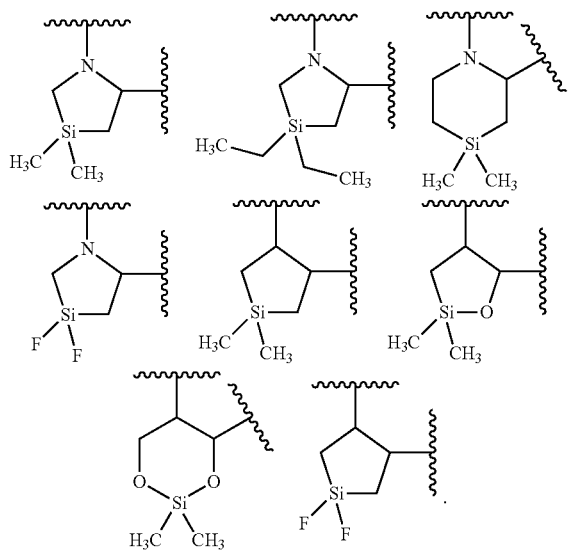

A ring carbon atom of a heterocycloalkyl group may be functionalized as a carbonyl group. An illustrative example of such a heterocycloalkyl group is:

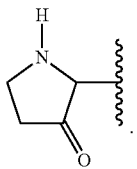

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different, and are each independently selected. Examples of ring system substituents include alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

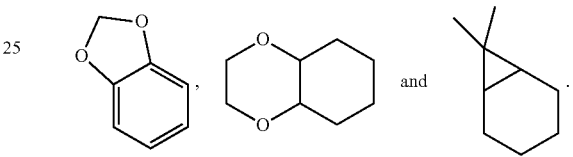

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., C$_1$-C$_6$ alkyl, R$^5$, R$^6$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a 2'-Alkynyl Substituted Nucleoside Derivative or a pharmaceutically acceptable salt of the compound. The transformation may occur by various mechanisms (e.g., by metabolic or chemical processes), such as, for example, through hydrolysis in blood.

For example, if a 2'-Alkynyl Substituted Nucleoside Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$ alkylcarbamoyl-$(C_1-C_2)$alkyl and piperidino-, pyrrolidino- or morpholino$(C_2-C_3)$alkyl, and the like.

Similarly, if a 2'-Alkynyl Substituted Nucleoside Derivative contains an alcohol functional group, a prodrug can be formed by the replacement of one or more of the hydrogen atoms of the alcohol groups with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$ alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate). Other non-limiting example of alcohol-derived prodrugs include —P(O)(OH)$_2$; —P(O)(—O—$C_1$-$C_6$alkyl)$_2$; —P(O)(—NH-(α-aminoacyl group))(-O-aryl); —P(O)(—O—$(C_1$-$C_6$ alkylene)-S-acyl)(-NH-arylalkyl); any cyclic phosphate ester that forms a bridge between two ribose hydroxyl groups, such as:

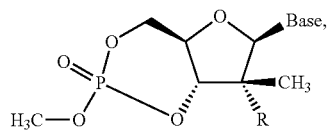

wherein the cyclic phosphate ester forms a bridge between the 3'-OH group and 5'-OH groups; and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842 (2005); Bobeck et al., *Antiviral Therapy* 15:935-950 (2010); Furman et al., Future Medicinal Chemistry, 1:1429-1452 (2009); and Erion, *Microsomes and Drug Oxidations, Proceedings of the International Symposium*, 17th, Saratoga Springs, N.Y., United States, July 6-10, 2008, 7-12 (2008).

If a 2'-Alkynyl Substituted Nucleoside Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$ alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino$(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Techours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The 2'-Alkynyl Substituted Nucleoside Derivatives can form salts which are also within the scope of this invention. Reference to a 2'-Alkynyl Substituted Nucleoside Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 2'-Alkynyl Substituted Nucleoside Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a 2'-Alkynyl Substituted Nucleoside Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the 2'-Alkynyl Substituted Nucleoside Derivatives may be atropisomers (e.g., substituted biaryls) and are considered as part of this invention. Enantiomers can also be directly separated using chiral chromatographic techniques.

It is also possible that the 2'-Alkynyl Substituted Nucleoside Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a 2'-Alkynyl Substituted Nucleoside Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the 2'-Alkynyl Substituted Nucleoside Derivatives, and of the salts, solvates, hydrates, esters and prodrugs of the 2'-Alkynyl Substituted Nucleoside Derivatives, are intended to be included in the present invention.

In some instances, the compounds of the present invention are designated as "isomer 1" and "isomer 2." This designation refers to stereoisomers at the chiral phosphorus atom of the 5'-prodrug moiety as illustrated below for cyclic and non-cyclic prodrugs, wherein the structure:

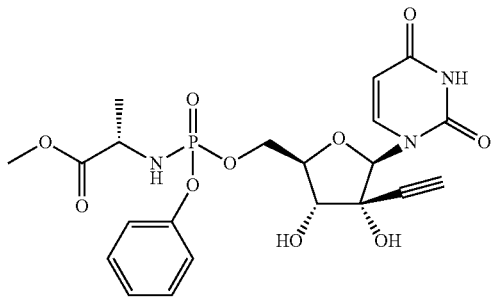 [SMILES: C#C[C@@]1(O)[C@H](O)[C@@H](COP(=O)(N[C@@H](C)C(=O)OC)Oc2ccccc2)O[C@H]1n1ccc(=O)[nH]c1=O]

is understood to represent the following two phosphorus stereoisomers:

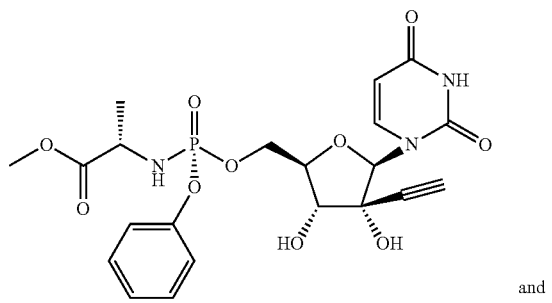

and the structure:

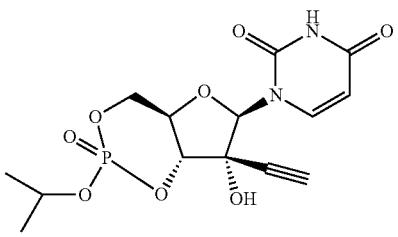

is understood to represent the following two phosphorus stereoisomers:

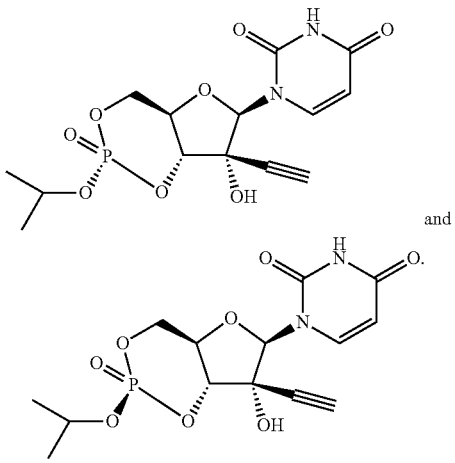

The terms "isomer 1" and "isomer 2" can be assigned to isomers of known absolute configuration or can be used to describe stereoisomers of unknown absolute configuration. Thus, the use of the terms "isomer 1" and "isomer 2" is not to be interpreted as indicating that the absolute configuration of both isomers is known.

The following abbreviations are used below and have the following meanings: Ac is acetyl or —C(O)CH$_3$, Bu is butyl; DMAP is N,N-dimethylamino pyridine; EDTA is ethylenediaminetetraacetic acid; DMSO is dimethylsulfoxide; EtOAc is ethyl acetate; EtOH is ethanol; HEPES is 4-(2-hydroxyethyl)-1-piperazineethanesulfonic acid; HPLC is high performance liquid chromatography; LiHMDS is lithium hexamethyldisilazide; MeOH is methanol; Ohira-Bestmann reagent is dimethyl 1-diazo-2-oxopropylphosphonate; Proton Sponge is 1,8-bis(dimethylamino)naphthalene; TBAF is tetra n-butylammonium fluoride; TEMPO is (2,2,6,6-Tetramethyl-piperidin-1-yl)oxyl; THF is tetrahydrofuran; and TLC is thin-layer chromatography.

The Compounds of Formula (I)

The present invention provides 2'-Alkynyl Substituted Nucleoside Derivatives of Formula (I):

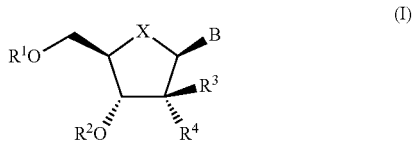

and pharmaceutically acceptable salts thereof, wherein B, X, $R^1$, $R^2$, $R^3$ and $R^4$ are defined above for the Compounds of Formula (I).

In one embodiment, X is O.
In another embodiment, X is N.
In another embodiment, X is S.
In another embodiment, X is CH$_2$.
In one embodiment, $R^3$ is —C≡CR$^5$.
In another embodiment, $R^3$ is —C≡CH, —C≡C—CH$_3$, —C≡C—CF$_3$ or —C≡CH-cyclopropyl.
In another embodiment, $R^3$ is —C≡CH.
In still another embodiment, $R^3$ is —C≡CH, —C≡C—CH$_3$, —C≡C—CF$_3$ or —C≡CH-cyclopropyl, and $R^4$ is —OH.

In another embodiment, R³ is —C≡CH, and R⁴ is —OH.

In one embodiment, R⁴ is —C≡CR⁵.

In another embodiment, R⁴ is —C≡CH, —C≡C—CH₃, —C≡C—CF₃ or —C≡CH-cyclopropyl.

In another embodiment, R⁴ is —C≡CH.

In still another embodiment, R⁴ is —C≡CH, —C≡C—CH₃, —C≡C—CF₃ or —C≡CH-cyclopropyl, and R³ is —OH.

In another embodiment, R⁴ is —C≡CH, and R³ is —OH.

In one embodiment, the compounds of formula (I) have the formula (Ia):

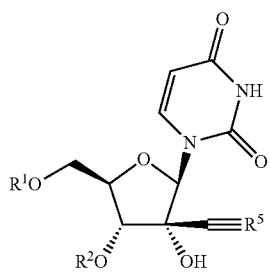

(Ia)

or a pharmaceutically acceptable salt thereof, wherein:

R¹ is H,

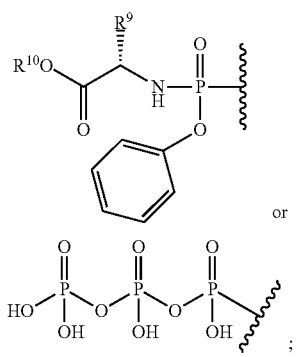

or

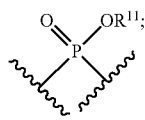

;

R² is H or —C(O)—(C₁-C₆ alkyl), or R¹ and R² join to form a group having the formula:

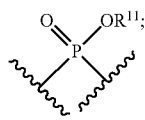

;

R⁵ is H or C₃-C₇ cycloalkyl;

R⁹ is C₁-C₆ alkyl;

R¹⁰ is C₁-C₆ alkyl; and

R¹¹ is C₁-C₆ alkyl.

In one embodiment, for the compounds of Formula (I) or Formula (Ia), B is:

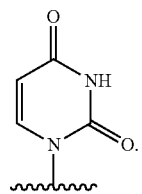 [SMILES: *n1ccc(=O)[nH]c1=O]

In another embodiment, for the compounds of Formula (I) or Formula (Ia), B is:

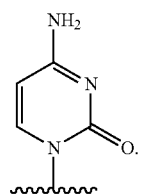 [SMILES: *n1ccc(N)nc1=O]

In one embodiment, for the compounds of formula (I) or (Ia), R¹ is H.

In another embodiment, for the compounds of formula (I) or (Ia), R¹ is

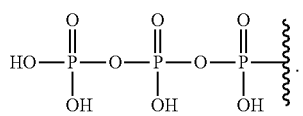 [SMILES: *P(=O)(O)OP(=O)(O)OP(=O)(O)O]

In another embodiment, for the compounds of formula (I) or (Ia), R¹ is

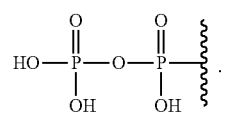

In still another embodiment, for the compounds of formula (I) or (Ia), R¹ is

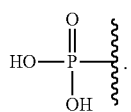

In one embodiment, for the compounds of Formula (I) or Formula (Ia), R¹ is:

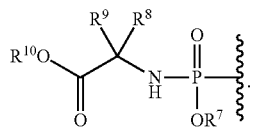

In another embodiment, for the compounds of Formula (I) or Formula (Ia), $R^1$ is:

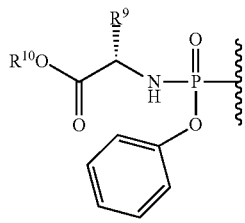

wherein $R^9$ and $R^{10}$ are each independently $C_1$-$C_6$ alkyl.

In another embodiment, for the compounds of Formula (I) or Formula (Ia), $R^1$ is

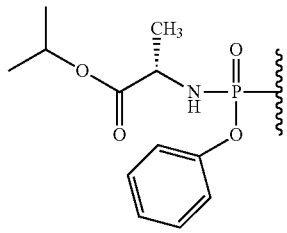

wherein $R^9$ and $R^{10}$ are each independently $C_1$-$C_6$ alkyl.

In another embodiment, for the compounds of Formula (I) or Formula (Ia), $R^1$ is

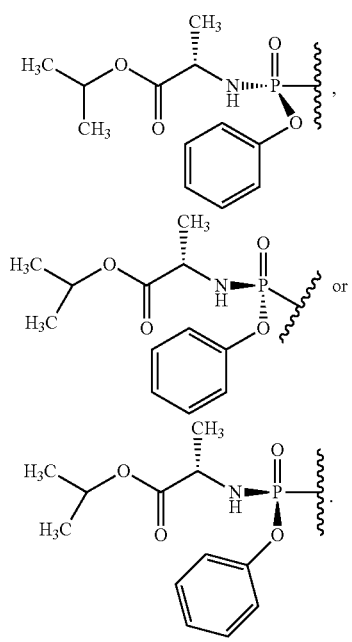

In one embodiment, for the compounds of Formula (I) or Formula (Ia), $R^2$ is H.

In another embodiment, for the compounds of Formula (I) or Formula (Ia), $R^2$ is —C(O)—($C_1$-$C_6$ alkyl).

In another embodiment, for the compounds of Formula (I) or Formula (Ia), $R^2$ is —C(O)—CH(CH$_3$)$_2$.

In one embodiment, for the compounds of formula (I) or (Ia), $R^1$ and $R^2$ join to form a group having the formula:

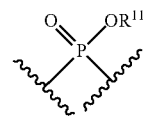

and $R^{11}$ is $C_1$-$C_6$ alkyl.

In another embodiment, for the compounds of formula (I) or (Ia), $R^1$ and $R^2$ join to form a group having the structure:

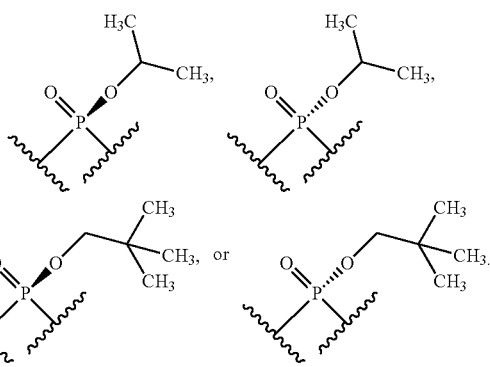

In another embodiment, for the compounds of formula (I) or (Ia), $R^1$ and $R^2$ join to form a group having the structure:

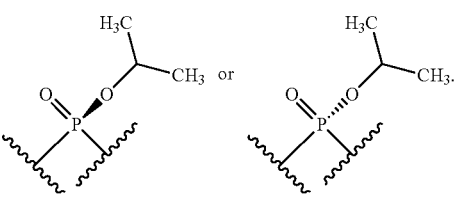

In one embodiment, for the compounds of Formula (I) or Formula (Ia), $R^2$ is H.

In another embodiment, for the compounds of Formula (I) or Formula (Ia), $R^2$ is —C(O)—($C_1$-$C_6$ alkyl).

In another embodiment, for the compounds of Formula (I) or Formula (Ia), $R^2$ is —C(O)—CH(CH$_3$)$_2$.

In one embodiment, variables B, X, $R^1$, $R^2$, $R^3$ and $R^4$ for the Compounds of Formula (I) are selected independently of each other.

In another embodiment, the Compounds of Formula (I) are in substantially purified form.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, HCV NS5B polymerase inhibitors and HCV NS5A inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors, HCV NS5B polymerase inhibitors and HCV NS5A inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors, HCV NS5B polymerase inhibitors and HCV NS5A inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

Additional embodiments of the invention include the pharmaceutical compositions, combinations and methods set forth in (a)-(k) above and the uses set forth in the discussion below, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

Uses of the 2'-Alkenyl Substituted Nucleoside Derivatives

The 2'-Alkynyl Substituted Nucleoside Derivatives are useful in the inhibition of HCV, the treatment of HCV infection and/or reduction of the likelihood or severity of symptoms of HCV infection and the inhibition of HCV viral replication and/or HCV viral production in a cell-based system. For example, the 2'-Alkynyl Substituted Nucleoside Derivatives are useful in treating infection by HCV after suspected past exposure to HCV by such means as blood transfusion, exchange of body fluids, bites, accidental needle stick, or exposure to patient blood during surgery or other medical procedures.

The present invention also includes a compound of the present invention for use (i) in, (ii) as a medicament for, or (iii) in the preparation of a medicament for: (a) medicine, (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators, as discussed in more detail, infra.

In one embodiment, the present invention includes the use of a compound of the present invention, or a pharmaceutically acceptable salt thereof, in a pharmaceutical composition for inhibiting HCV NS5B activity or for preventing and/or treating infection by HCV in a patient in need thereof.

In accordance with the invention, the 2'-Alkynyl Substituted Nucleoside Derivatives can be administered to a patient in need of treatment or prevention of a viral infection. Accordingly, in one embodiment, the invention provides methods for treating a viral infection in a patient comprising administering to the patient an effective amount of at least one 2'-Alkynyl Substituted Nucleoside Derivative or a pharmaceutically acceptable salt thereof.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one 2'-Alkynyl Substituted Nucleoside Derivative or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The 2'-Alkynyl Substituted Nucleoside Derivatives are also useful in the preparation and execution of screening assays for antiviral compounds. For example the 2'-Alkynyl Substituted Nucleoside Derivatives are useful for identifying resistant HCV replicon cell lines harboring mutations within NS5B, which are excellent screening tools for more powerful antiviral compounds. Furthermore, the 2'-Alkynyl Substituted Nucleoside Derivatives are useful in establishing or determining the binding site of other antivirals to the HCV NS5B polymerase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b.

Combination Therapy

In another embodiment, the present methods for treating or preventing HCV infection can further comprise the administration of one or more additional therapeutic agents which are not 2'-Alkynyl Substituted Nucleoside Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one 2'-Alkynyl Substituted Nucleoside Derivative (which may include two or more different 2'-Substituted Nucleoside Derivatives), or a pharmaceutically acceptable salt thereof, and (ii) at least one additional therapeutic agent that is other than a 2'-Alkynyl Substituted Nucleoside Derivative, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 2'-Alkynyl Substituted Nucleoside Derivative and an additional therapeutic agent may be present in fixed amounts (dosage amounts) in a single dosage unit (e.g., a capsule, a tablet and the like).

In one embodiment, the at least one 2'-Alkynyl Substituted Nucleoside Derivative is administered during a time when the additional therapeutic agent(s) exert their prophylactic or therapeutic effect, or vice versa.

In another embodiment, the at least one 2'-Alkynyl Substituted Nucleoside Derivative and the additional therapeutic agent(s) are administered in doses commonly employed when such agents are used as monotherapy for treating a viral infection.

In another embodiment, the at least one 2'-Alkynyl Substituted Nucleoside Derivative and the additional therapeutic agent(s) are administered in doses lower than the doses commonly employed when such agents are used as monotherapy for treating a viral infection.

In still another embodiment, the at least one 2'-Alkynyl Substituted Nucleoside Derivative and the additional therapeutic agent(s) act synergistically and are administered in doses lower than the doses commonly employed when such agents are used as monotherapy for treating a viral infection.

In one embodiment, the at least one 2'-Alkynyl Substituted Nucleoside Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one 2'-Alkynyl Substituted Nucleoside Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one 2'-Alkynyl Substituted Nucleoside Derivative and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, one or more compounds of the invention are administered with one or more additional therapeutic agents, including but not limited to the therapeutic agents described, supra.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor.

In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In another embodiment, one or more compounds of the present invention are administered with one additional therapeutic agent selected from an HCV protease inhibitor, an interferon, a pegylated interferon and ribavirin. In another embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759/VX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125; and the following compounds:

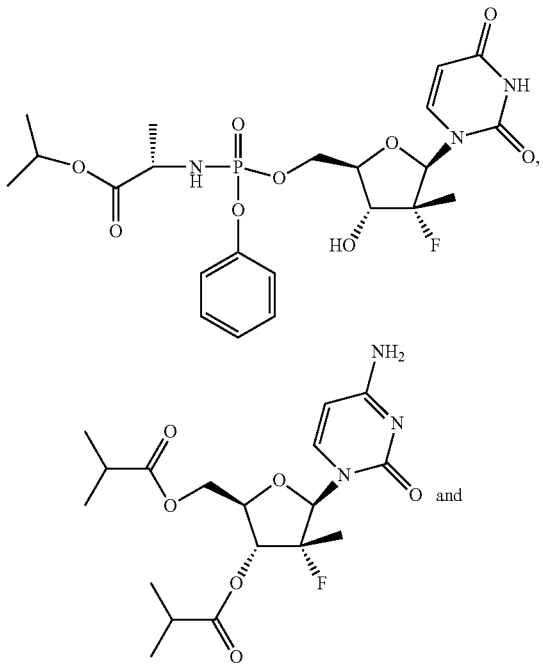

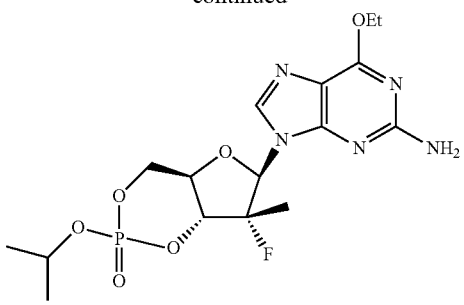

and pharmaceutically acceptable salts thereof.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of viral protease inhbitors useful in the present compositions and methods include, but are not limited to, an HCV protease inhibitor. Examples of HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, the following compounds:

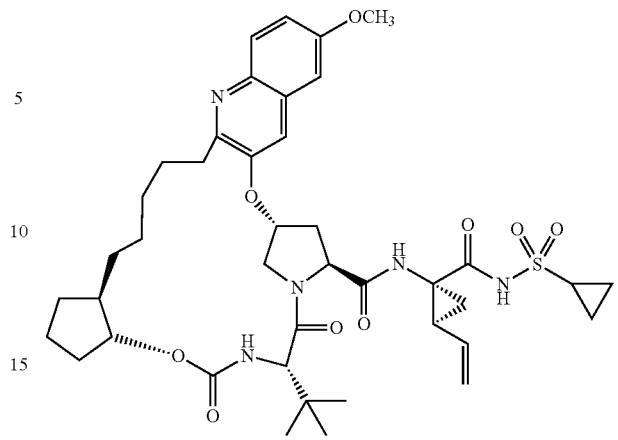

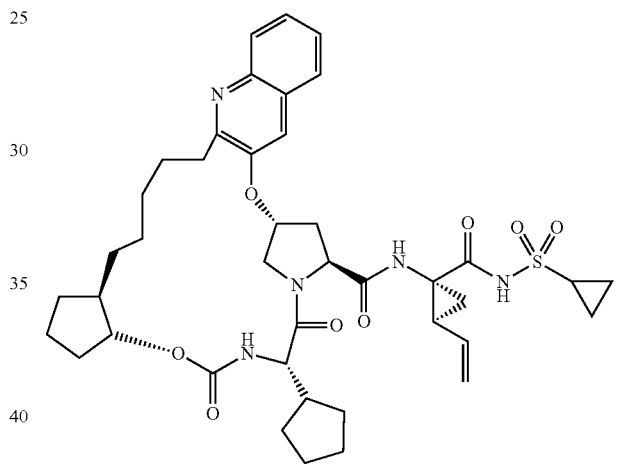

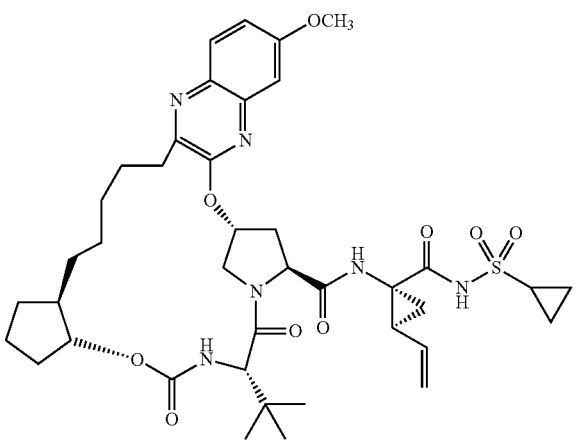

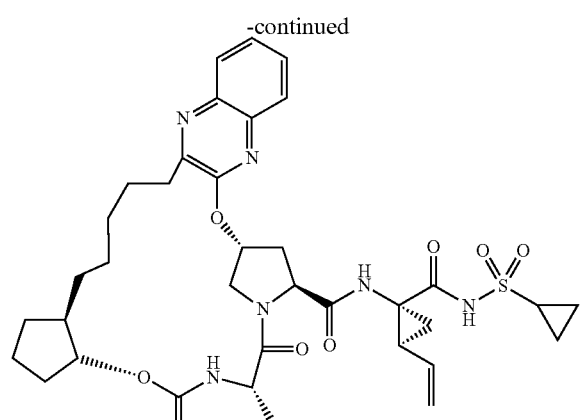
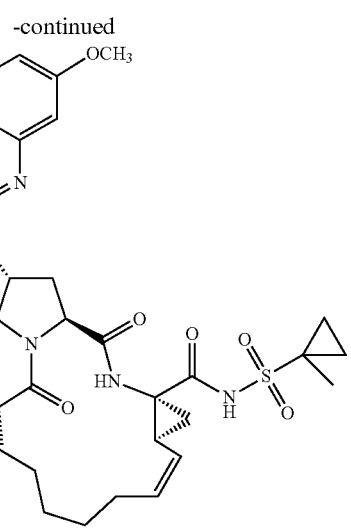
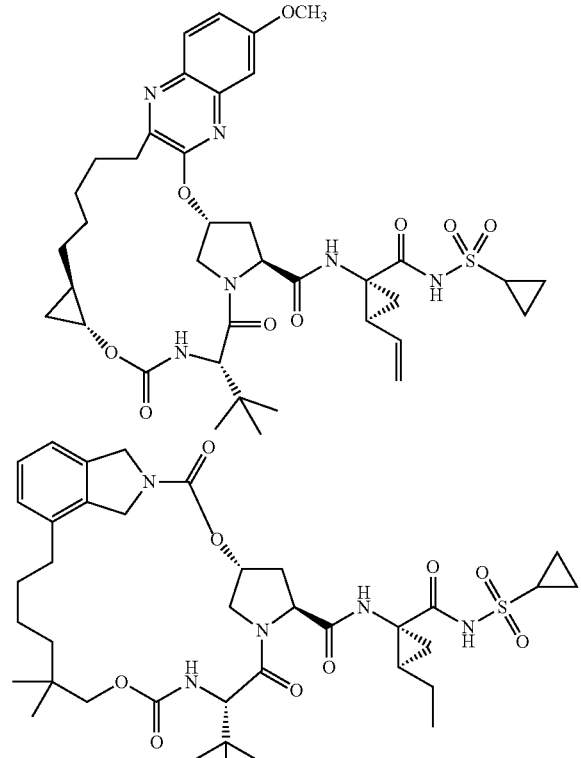
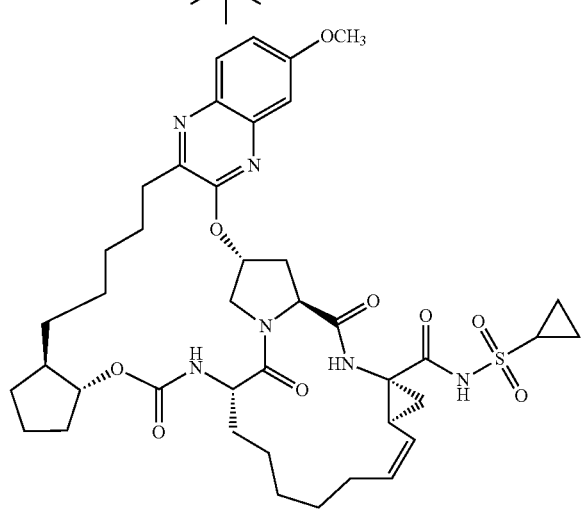

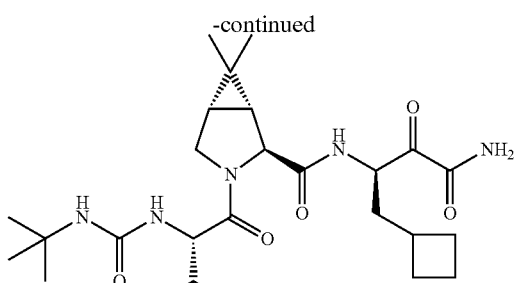
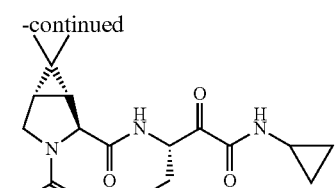
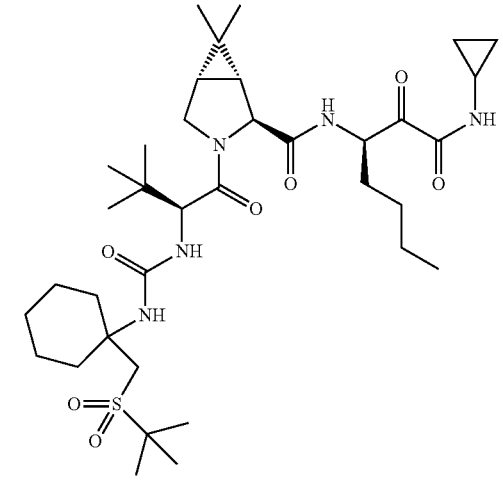
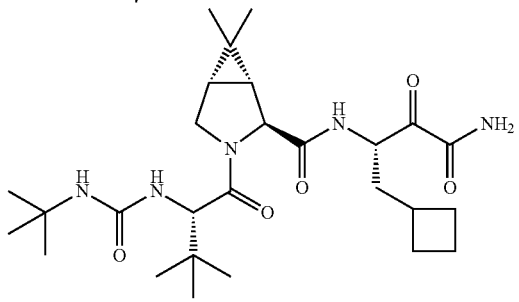
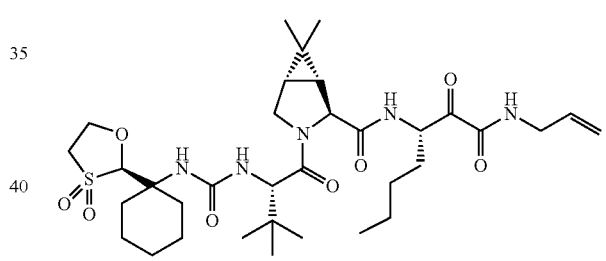
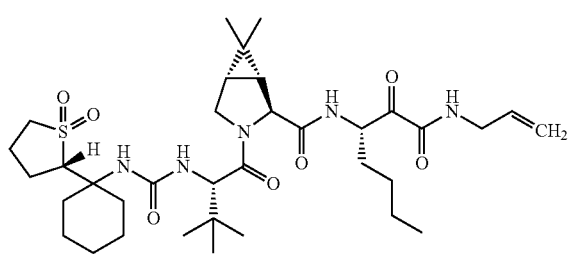
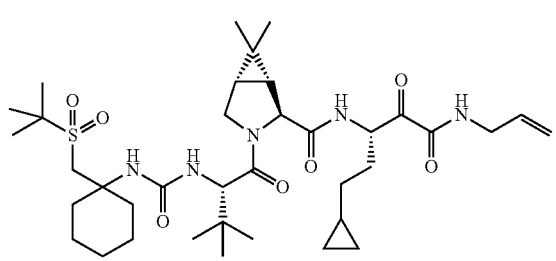

-continued

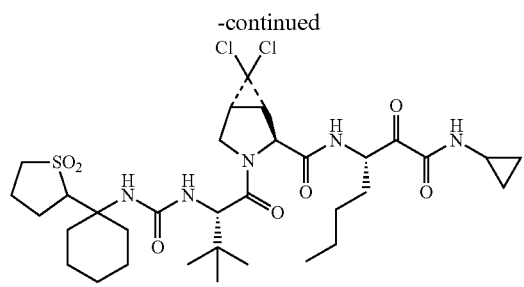

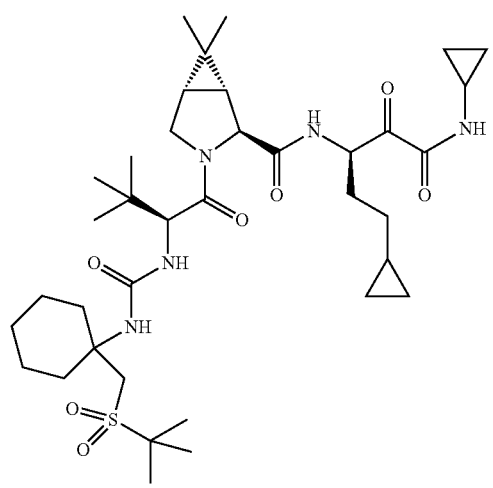

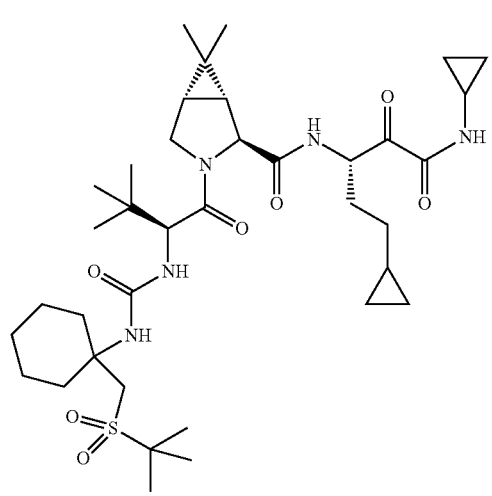

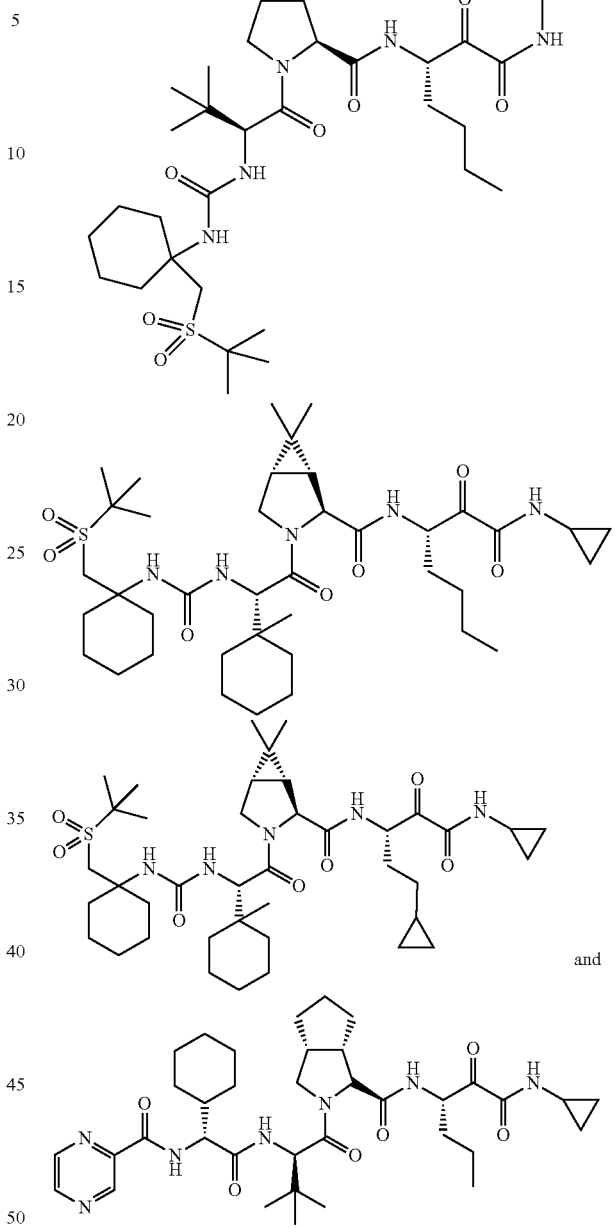

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), PPI-461 (Presidio), PPI-1301 (Presidio), BMS-824383 (Bristol-Myers Squibb) and BMS-790052 (Bristol-Myers Squibb). Additional HCV NS5A inhibitors useful as second additional therapeutic agents in the present compositions and methods include, but are not limited to those disclosed in International Publication No. WO 2010/111483 and the following compounds:
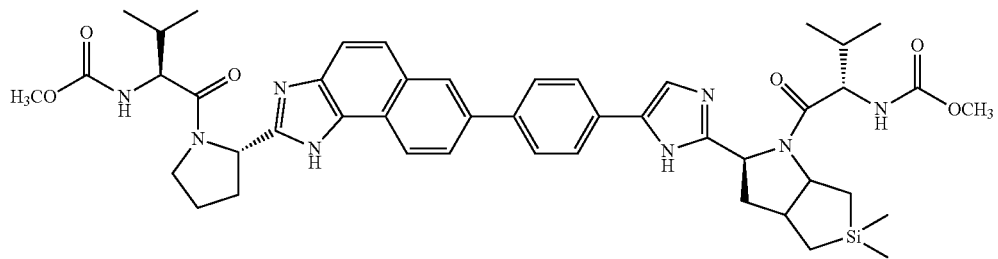
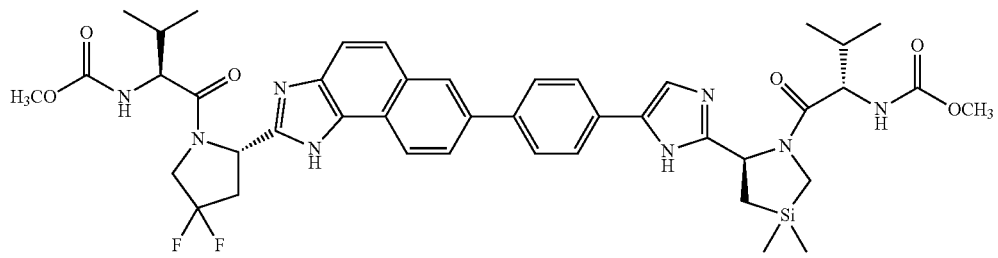
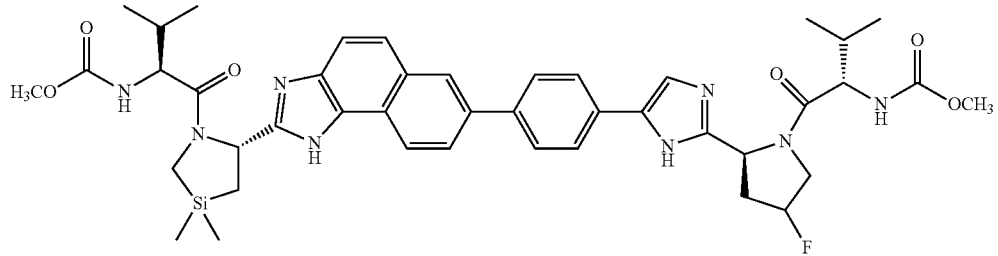
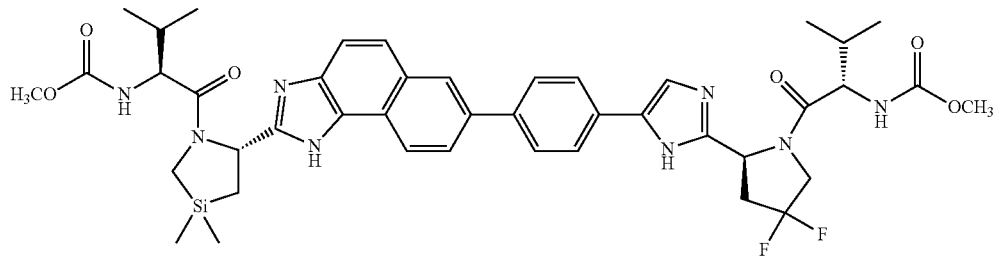
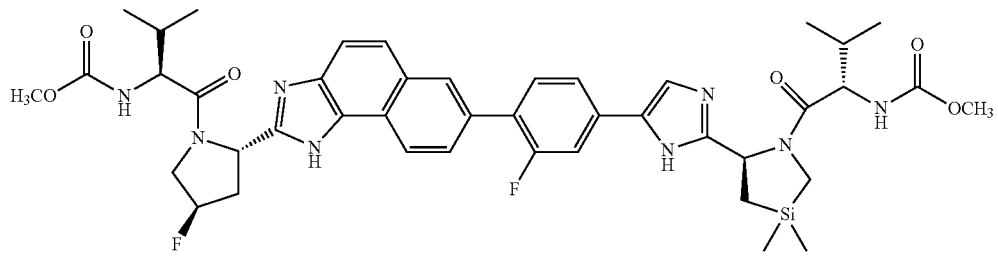
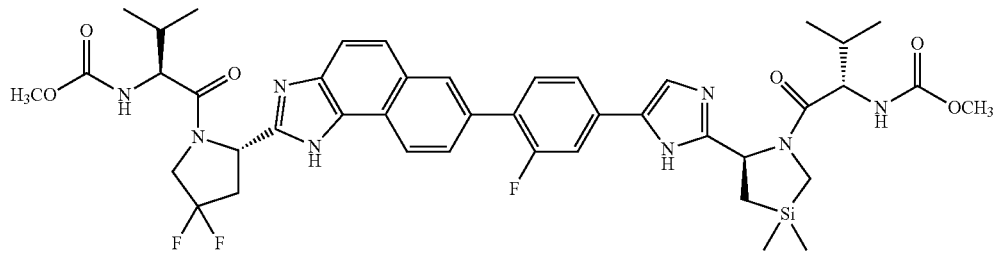

-continued
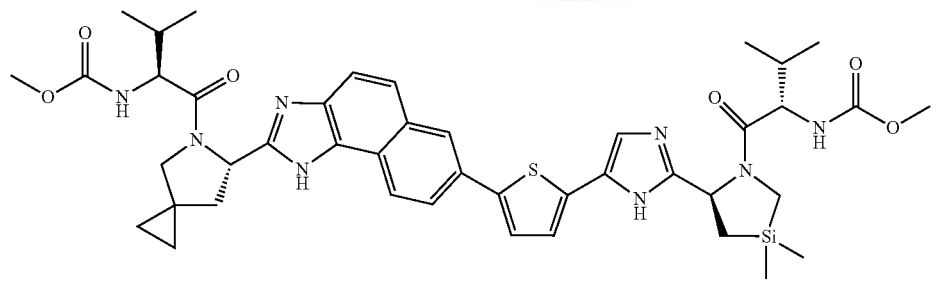
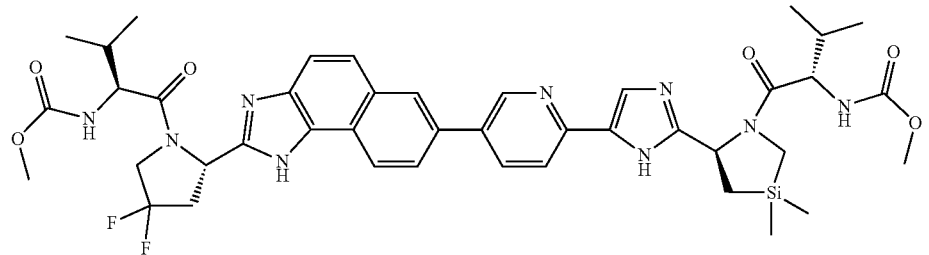
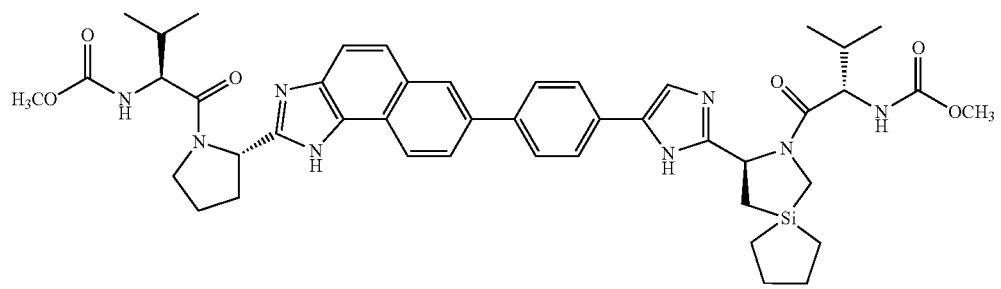
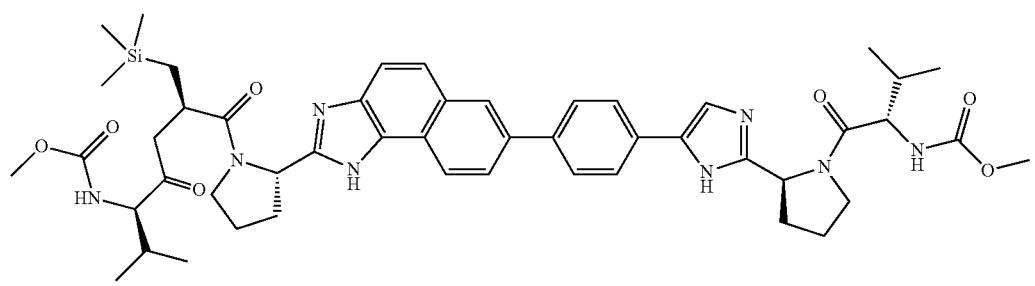
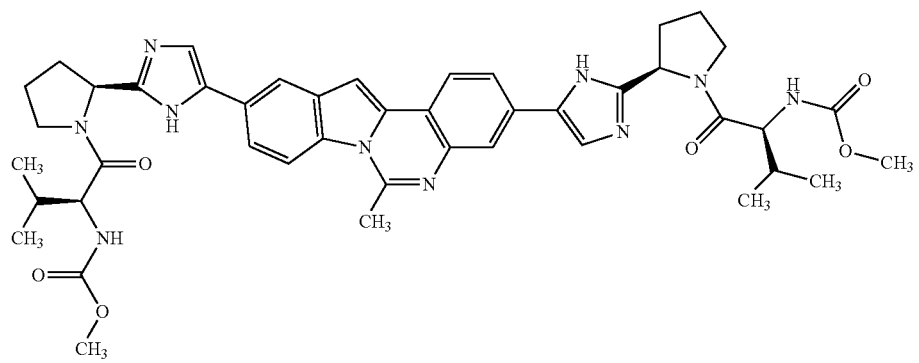

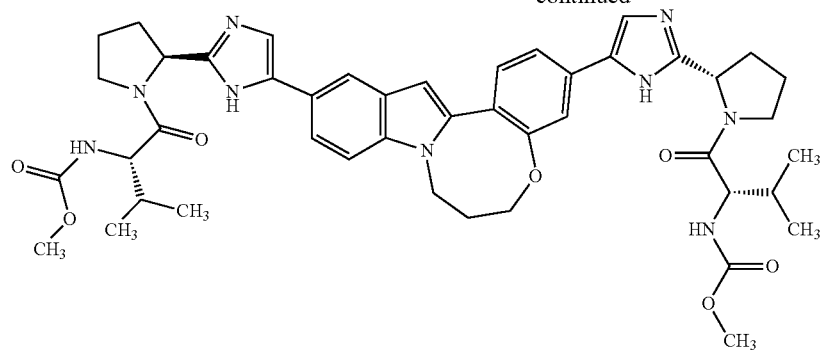
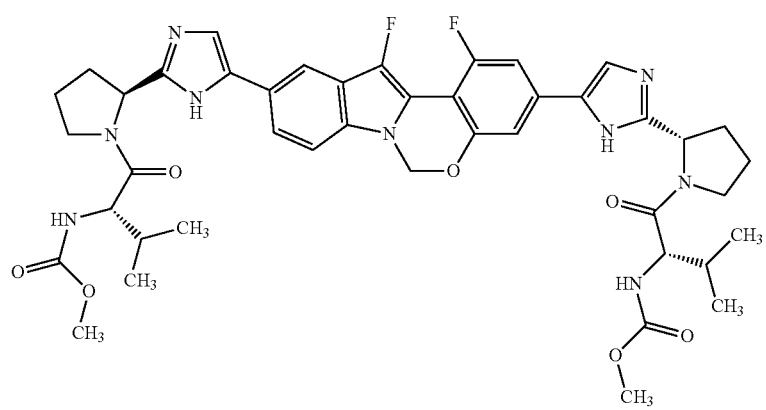
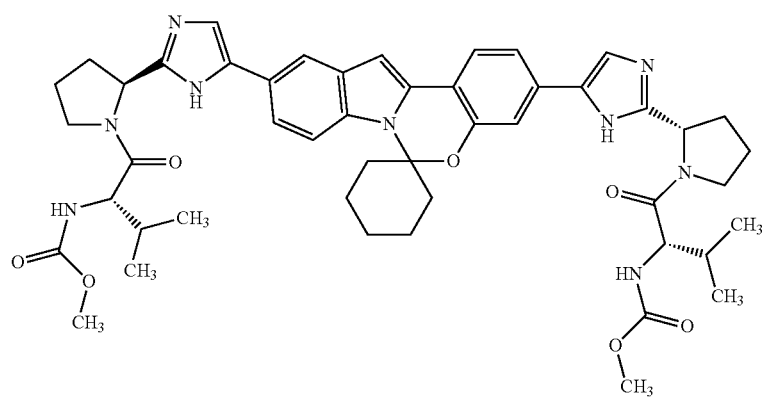
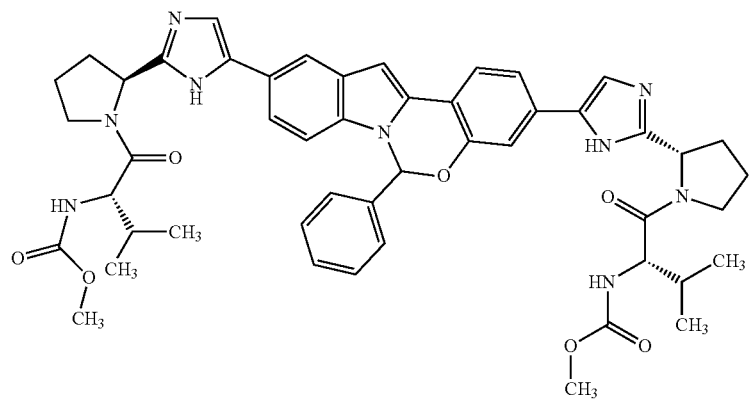

-continued
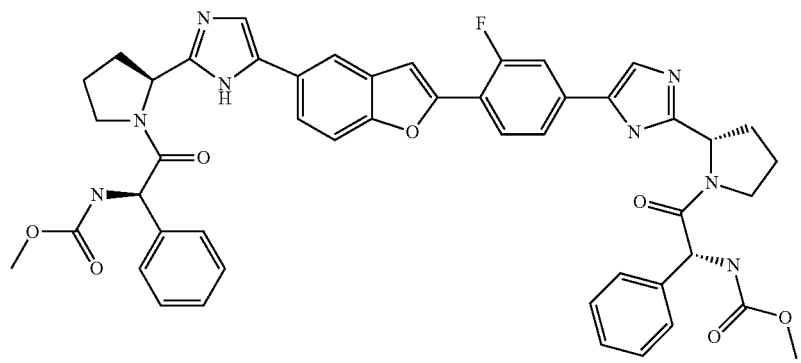
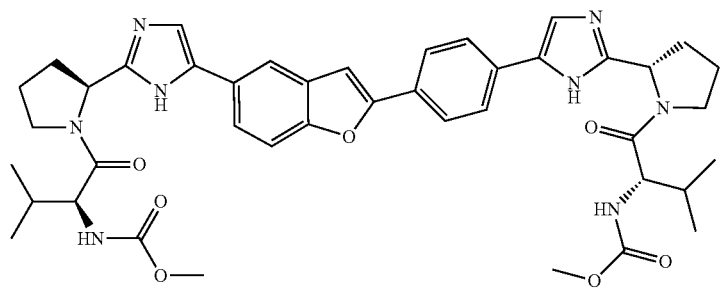
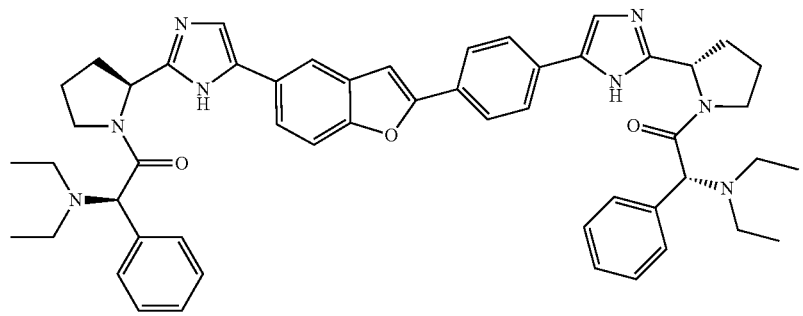
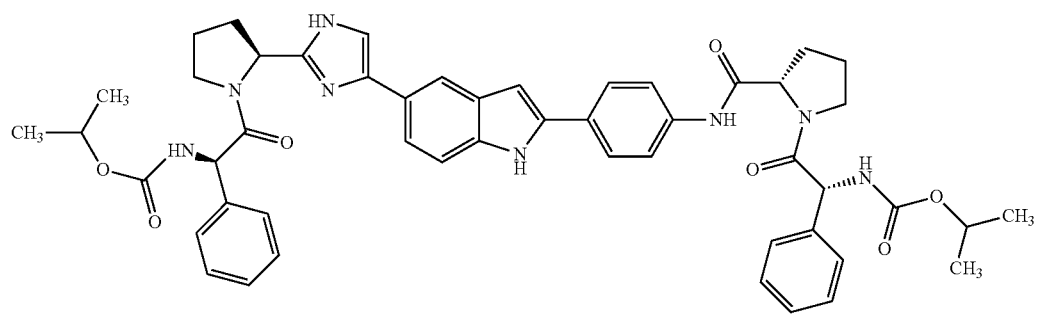
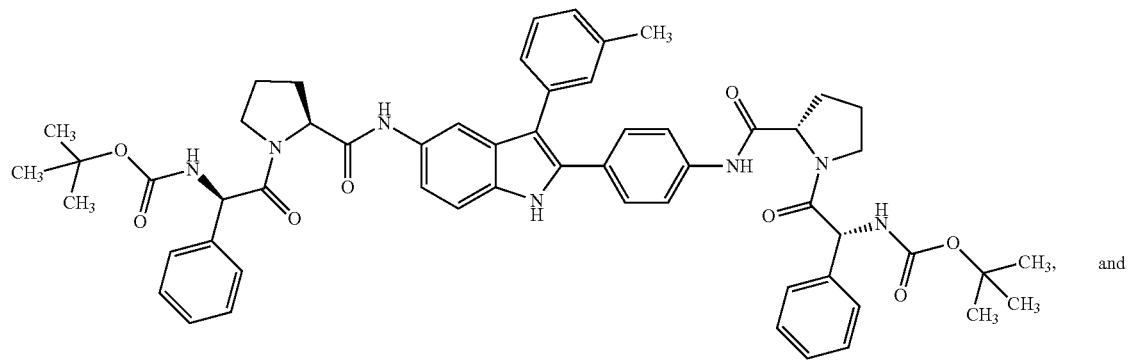
and

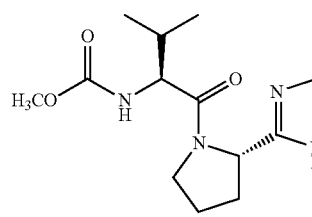 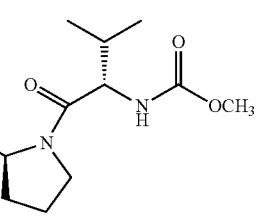

and pharmaceutically acceptable salts thereof.

HCV replicase inhibitors useful in the present compositions and methods include, but are not limited to, those disclosed in U.S. Patent Publication No. US20090081636.

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the 2'-Alkynyl Substituted Nucleoside Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one 2'-Alkynyl Substituted Nucleoside Derivative(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the 2'-Alkynyl Substituted Nucleoside Derivatives are useful in veterinary and human medicine. As described above, the 2'-Alkynyl Substituted Nucleoside Derivatives are useful for treating or preventing HCV infection in a patient in need thereof.

When administered to a patient, the 2'-Alkynyl Substituted Nucleoside Derivatives can be administered as a component of a composition that comprises a pharmaceutically acceptable carrier or vehicle. The present invention provides pharmaceutical compositions comprising an effective amount of at least one 2'-Alkynyl Substituted Nucleoside Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 2'-Alkynyl Substituted Nucleoside Derivatives are administered orally.

In another embodiment, the one or more 2'-Alkynyl Substituted Nucleoside Derivatives are administered intravenously.

In one embodiment, a pharmaceutical preparation comprising at least one 2'-Alkynyl Substituted Nucleoside Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the 2'-Alkynyl Substituted Nucleoside Derivative(s) by weight or volume. In various embodiments, the present compositions can contain, in one embodiment, from about 1% to about 70% or from about 5% to about 60% of the 2'-Alkynyl Substituted Nucleoside Derivative(s) by weight or volume.

The quantity of 2'-Alkynyl Substituted Nucleoside Derivative in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 2'-Alkynyl Substituted Nucleoside Derivatives will be regulated according to the judgment of the attending clinician considering such factors as age, condition and size of the patient as well as severity of the symptoms being treated. Generally, a total daily dosage of the 2'-Alkynyl Substituted Nucleoside Derivatives range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 2'-Alkynyl Substituted Nucleoside Derivative or a pharmaceutically acceptable salt thereof; (ii) one or more additional therapeutic agents that are not a 2'-Alkynyl Substituted Nucleoside Derivative; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and two additional therapeutic agents, each of which are independently selected from the group consisting of HCV antiviral agents, immunomodulators, and anti-infective agents.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Scheme 1 below. Alternative synthetic pathways and analogous structures will be apparent to those skilled in the art of organic synthesis.

Scheme 1 below shows a method for making the Compounds of Formula (I), wherein $R^3$ and $R^4$ are each —C≡C—$R^5$.

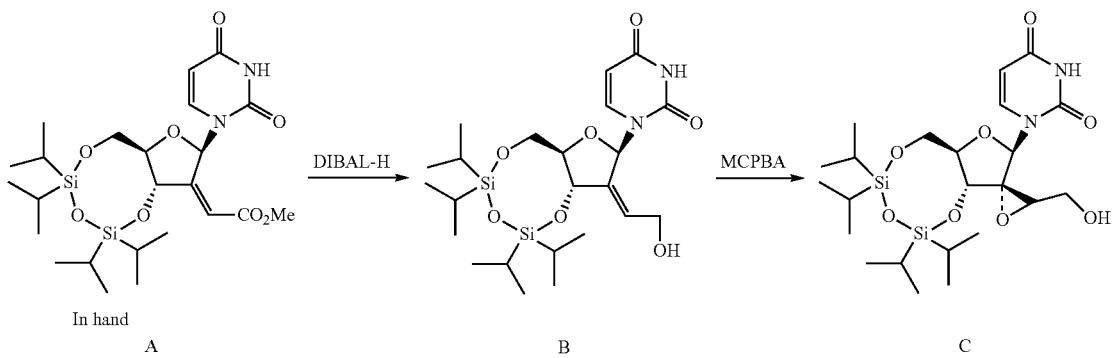

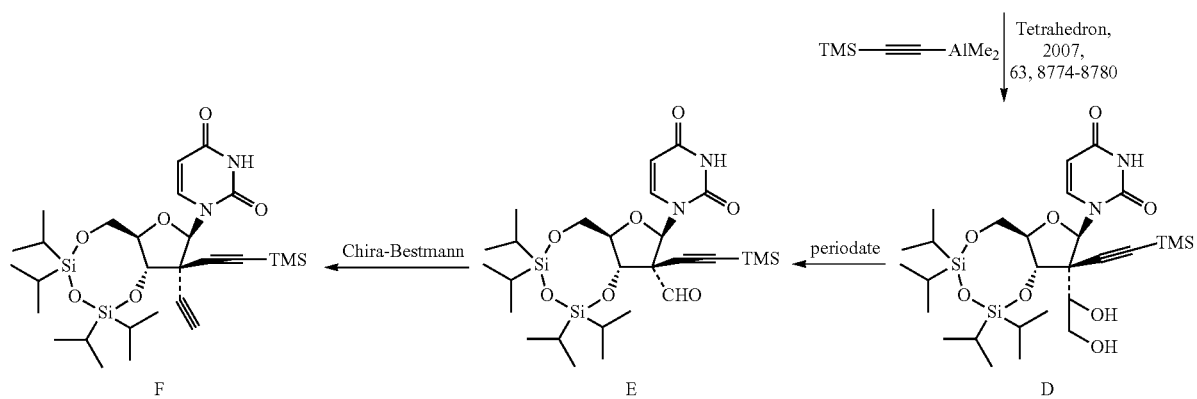

A compound of formula A can be reduced using DIBAL-H to provide the allylic alcohol of formula B. Sharpless-type epoxidation the olefin in B using mCPBA, for example, provides the epoxide of formula C. Alknylation of the olefinic moiety of C provided the alkynyl diol of formula D, which can then be oxidized using periodate to provide the alkynyl aldehyde of formula E. Reaction of the aldehyde moiety of E with the Ohira-Bestmann reagent provides the di-alkynyl compounds of formula F, which can be further elaborated to provide the Compounds of Formula (I), wherein $R^3$ and $R^4$ are each —C≡C—$R^5$.

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

The starting materials used and the intermediates prepared using the methods set forth in Scheme 1 may be isolated and purified if desired using conventional techniques, including but not limited to filtration, distillation, crystallization, chromatography and alike. Such materials can be characterized using conventional means, including physical constants and spectral data.

Non-limiting examples of the Compounds of Formula (I) include compounds 1-32 as set forth in the Examples below, and pharmaceutically acceptable salts thereof.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from $Me_4Si$ with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes-10% $CH_3CN$, 5 minutes-95% $CH_3CN$, 5-7 minutes-95% $CH_3CN$, 7 minutes-stop. The parent ion is given. Flash chromatography on silica gel was performed using pre-packed normal phase silica from Isco, Biotage, Inc. or bulk silica from Fisher Scientific. Unless otherwise indicated, flash chromatography on silica gel was performed using a gradient elution of hexanes/ethyl acetate, from 100% hexanes to 100% ethyl acetate.

Example 1

Preparation of Intermediate Compounds Int-1d and Int-1e

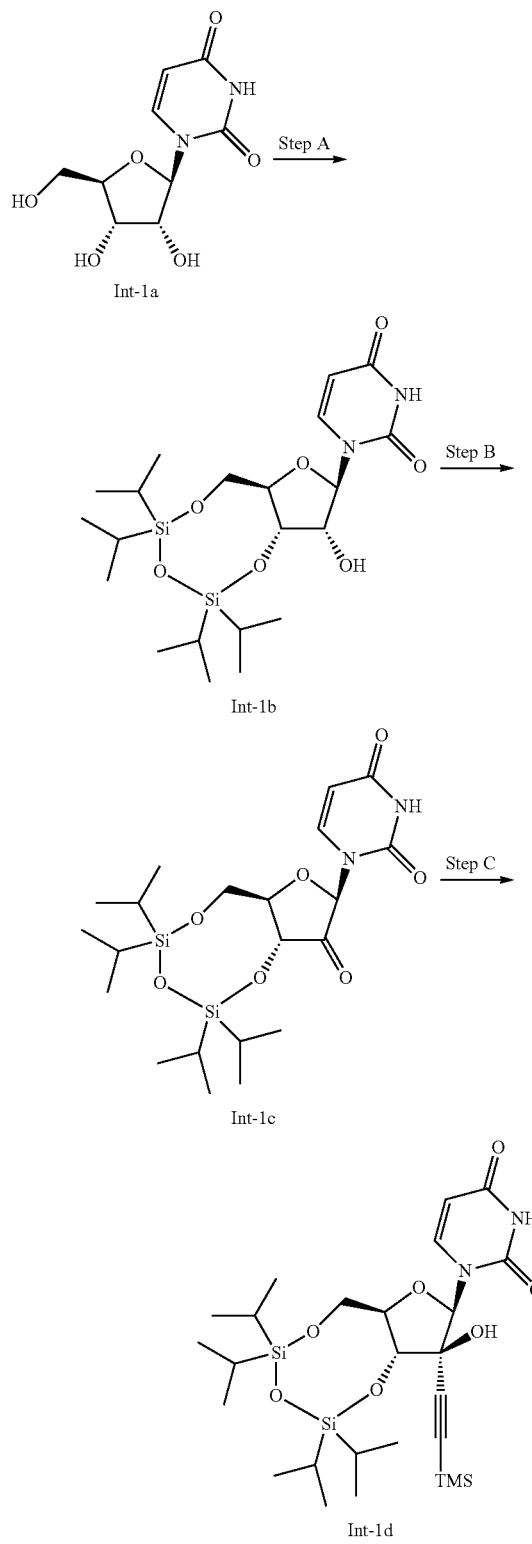

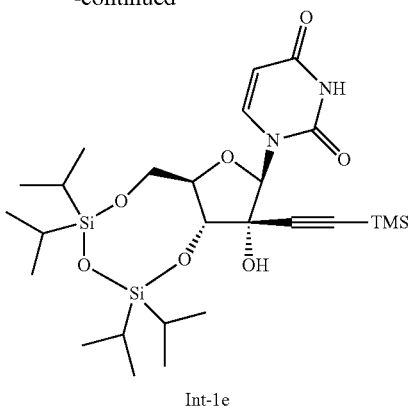

Int-1e

Step 1A—Synthesis of Compound Int-1b

Uridine (Int-1a, 10.0 g, 40.9 mmol) was azeotroped with pyridine (50 mL) and then dissolved in pyridine (50 mL). To the solution was added tetraisopropyldisiloxanedichloride (15.0 mL, 40.9 mmol) dropwise and the resulting reaction was allowed to stir overnight at room temperature. The reaction mixture was partitioned between EtOAc and 10% aq. HCl. The organic phase was separated, washed with an additional portion of 10% aq. HCl, washed with brine, dried (MgSO4) and the volatiles removed under reduced pressure to give the desired protected nucleoside Int-1b (19.89 g; 100%) as a white solid. Used without purification. [M+H]=487.43.

Step 1B—Synthesis of Compound Int-1c

Compound Int-1b (25.01 g, 51.4 mmol) was dissolved in dichloromethane (122 mL) and potassium bromide (0.947 g; 7.96 mmol) followed by TEMPO (1.243 g; 7.96 mmol) were added. Finally, sodium bicarbonate (13.37 g; 159 mmol) in water (80 mL). The resulting mixture was vigorously stirred and placed in an ice bath. Aqueous sodium hypochlorite (6%; 122 mL) was added dropwise. The resulting reaction mixture was stirred while cooled in the ice bath for a further 1 h. and then partitioned between EtOAc and 10% aq. sodium thiosulfate. The organic phase was separated, washed with additional 10% aq. sodium thiosulfate, 10% aq. HCl (×2), brine, dried (MgSO4) and the volatiles were removed under reduced pressure to give the desired ketone Int-1c, (26.22 g; 105%), which was used without further purification. [M+H]=485.20.

Step 1C—Synthesis of Compound Int-1d and Compound Int-1e

Ethynyltrimethylsilane (9.12 g; 93 mmol) was weighed directly into a 500 mL round bottom flask and anhydrous THF (100 mL) was added and the solution was cooled to −78 C, under an atmosphere of nitrogen. N-Butyllithium (58 mL of a 1.6M solution in hexanes; 93 mmol) was added dropwise and the resulting mixture was stirred at this temperature for 30 min. The crude ketone Int-1c (15.0 g; 30.9 mmol) in anhydrous THF (40 mL) was added dropwise. When the addition was complete stirring was continued at −78 C for a period of 3 h. Sat. aq column chromatography using 0 to 25% EtOAc in hexanes as eluent. Gave Int-1d (10.31 g; 57.2%) as a white foam. [M+H]=583.29 followed by Int-1e (1.29 g; 7.15%) also a white foam [M+H]=583.30.

Example 2

Preparation of Compound 1

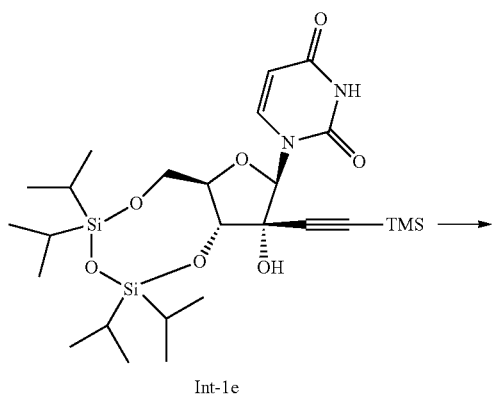

Int-1e

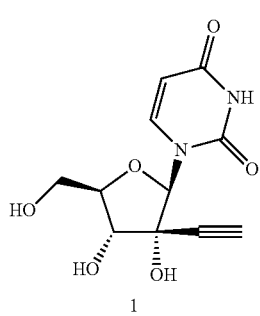

1

Tetrabutylammonium fluoride (1.34 mL of a 1M solution in THF; 1.34 mmol) was added to a solution of the silyl ether Int-1e (0.380 g; 0.688 mmol) in THF (4 mL) and the resulting reaction mixture was stirred at room temperature for 1 h. The volatiles were removed under reduced pressure and the residue was purified using silica gel column chromatography using a gradient of 0 to 10% methanol in dichloromethane as eluent. This provided the desired triol 1 (0.070 g; 38%) as a white solid. [M+H]=269.09. $^1$H NMR (DMSO-$d_6$) δ: 11.31 (br. s., 1H), 7.93 (d, J=7.9 Hz, 1H), 6.15 (s, 1H), 5.85 (s, 1H), 5.68 (d, J=7.0 Hz, 1H), 5.60 (d, J=7.9 Hz, 1H), 5.21 (br. s., 1H), 4.00 (t, J=7.9 Hz, 1H), 3.75 (br. s., 2H), 3.57 (d, J=11.9 Hz, 1H), 3.45 (s, 1H). $^{13}$C NMR (DMSO-$d_6$) δ: 162.8, 147.1, 139.9, 101.0, 90.0, 81.8, 81.7, 76.9, 75.3, 73.3, 58.3.

Example 3

Preparation of Compound 11

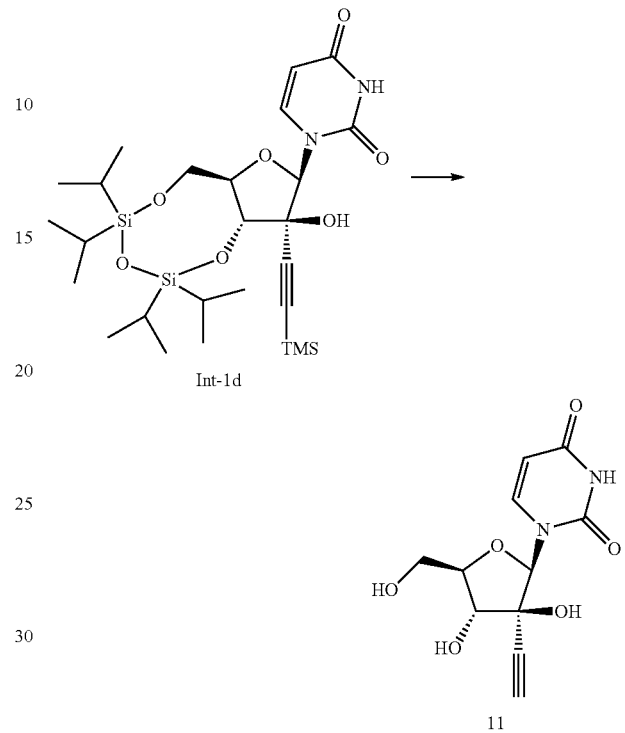

Int-1d

11

Tetrabutylammonium fluoride (51.5 mL of a 1M solution in THF; 51.5 mmol) was added to the silyl ether Int-1d (10.0 g; 17.16 mmol) and the resulting reaction mixture was stirred at room temperature for 1 h. The volatiles were removed under reduced pressure and the residue was purified using silica gel column chromatography using a gradient of 0 to 10% methanol in dichloromethane as eluent. This provided the desired triol 11 (2.60 g; 56.5%) as a white solid. [M+H]=269.23.
$^1$H NMR (DMSO-$d_6$) δ: 11.29 (br. s., 1H), 7.65 (d, J=8.2 Hz, 1H), 6.42 (s, 1H), 6.08 (s, 1H), 5.83 (d, J=5.7 Hz, 1H), 5.57 (dd, J=8.2 and 1.8 Hz, 1H), 5.08 (t, J=5.4 ractions, 1H), 3.84 (t, J=5.1 Hz, 1H), 3.75 (q, J=4.7, 1H), 3.50-3.65 (m, 2H), 3.52 (s, 1H). $^{13}$C NMR (DMSO-$d_6$) δ: 163.1, 150.5, 142.4, 100.3, 86.7, 84.2, 81.5, 78.6, 77.0, 75.7, 60.7.

Example 4

Preparation of Compound 2

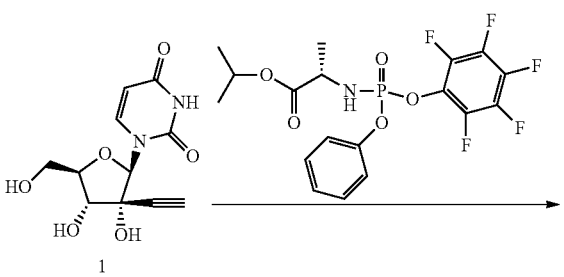

1

-continued

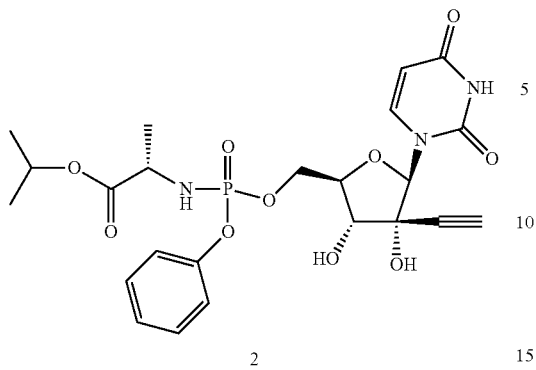

2

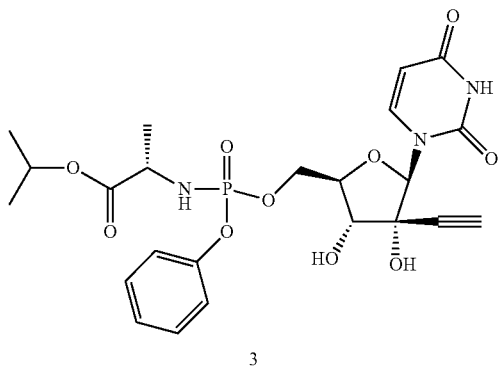

3

Tert-Butylmagnesium chloride (2.237 mL of a 1.0M solution in THF; 2.237 mmol) was added dropwise to a stirred solution of the nucleoside 1 (0.200 g; 0.746 mmol) in anhydrous THF (1 mL). while cooled in an ice bath, under an atmosphere of nitrogen. The resulting mixture was stirred for 10 min. and a solution of the pentafluorophenyl ester (0.406 g; 0.895 mmol) in anhydrous THF (1 mL) was added. The resulting reaction mixture was allowed to warm to room temperature overnight. The reaction was quenched with saturated aqueous ammonium chloride and then partitioned between EtOAc and sat. aq. ammonium chloride. The organic phase was separated, dried ($MgSO_4$) and the volatiles removed under reduced pressure. The residue was purified using silica gel column chromatography using a gradient of 0 to 10% MeOH in dichloromethane as eluent. This provided the desired phosphate 2 (0.180 g; 44.9%) as a white solid. [M+H]=538.43

$^1$H NMR (500 MHz, $CD_3OD$): δ 7.63 (d; J=8.13 Hz; 1H); 7.35 (t; J=7.82 Hz; 2H); 7.24 (d; J=8.11 Hz; 2H); 7.18 (t; J=7.38 Hz; 1H); 6.01 (s; 1H); 5.59 (d; J=8.12 Hz; 1H); 4.93-4.94 (m; 1H); 4.45-4.46 (m; 1H); 4.33-4.34 (m; 1H); 4.14 (d; J=9.06 Hz; 1H); 4.06 (d; J=8.67 Hz; 1H); 3.90 (dd; J=9.86; 7.00 Hz; 1H); 3.06 (s; 1H); 1.33 (d; J=7.14 Hz; 3H); 1.20 (dd; J=6.27; 2.20 Hz; 6H).

Example 5

Preparation of Compound 3

Tert-Butylmagnesium chloride (3.355 mL of a 1.0M solution in THF; 3.355 mmol) was added dropwise to a stirred solution of the nucleoside 1 (0.300 g; 1.118 mmol) in anhydrous THF (1 mL). while cooled in an ice bath, under an atmosphere of nitrogen. The resulting mixture was stirred for 10 min. and a solution of the pentafluorophenyl ester (0.608 g; 1.342 mmol) in anhydrous THF (1 mL) was added. The resulting reaction mixture was allowed to warm to room temperature overnight. The reaction was quenched with saturated aqueous ammonium chloride and then partitioned between EtOAc and sat. aq. ammonium chloride. The organic phase was separated, dried ($MgSO_4$) and the volatiles removed under reduced pressure. The residue was purified using silica gel column chromatography using a gradient of 0 to 10% MeOH in dichloromethane as eluent. This provided the desired phosphate 3 (0.193 g; 32.1%) as a white solid. [M+H]=538.47

$^1$H NMR (500 MHz, $CD_3OD$): δ 7.63 (d; J=8.11 Hz; 1H); 7.34 (t; J=7.77 Hz; 2H); 7.18-7.20 (m; 3H); 6.02 (s; 1H); 5.60 (d; J=8.12 Hz; 1H); 4.94-4.95 (m; 1H); 4.52 (dd; J=12.76; 4.99 Hz; 1H); 4.36 (ddd; J=11.81; 5.56; 3.04 Hz; 1H); 4.13 (d; J=9.04 Hz; 1H); 4.05-4.08 (m; 1H); 3.86-3.88 (m; 1H); 3.03 (s; 1H); 1.28 (d; J=7.23 Hz; 3H); 1.19 (t; J=5.84 Hz; 6H)

Example 6

Preparation of Compound 4

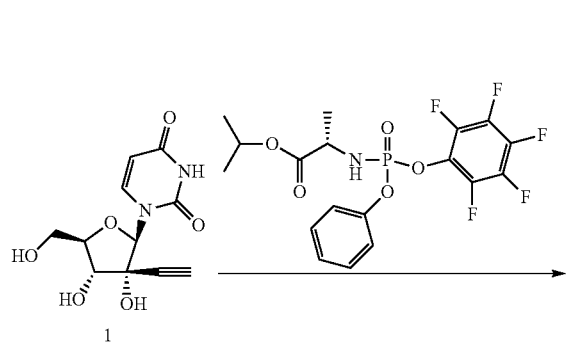

1

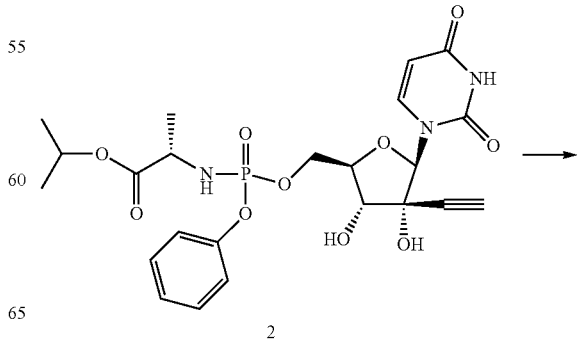

2

-continued

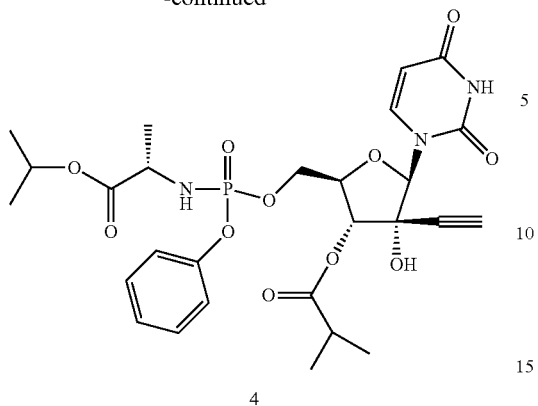

4

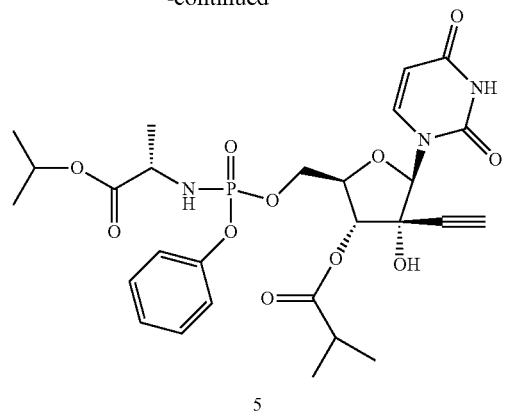

5

Isobutyryl chloride (0.043 mL; 0.409 mmol; 2 eq) was added, slowly, to a mixture of the phosphate 2 (0.110 g; 0.205 mmol), triethylamine (0.086 mL; 0.614 mmol) and DMAP (0.003 g; 0.025 mmol) in THF (5 mL) and water (5 mL) while cooled in an ice bath After a period of 1 h., an additional portion of isobutyryl chloride (0.5 eq) was added. After stirring for an additional 15 min., the reaction was acidified to pH=6-7 with aqueous HCl and the organics extracted into EtOAc twice. The combined organic phases were washed with water, washed with brine, dried (MgSO4) and the volatiles removed under reduced pressure. The residue was purified using silica gel column chromatography using 0 to 10% MeOH in dichloromethane as eluent. This provided the desired phosphate 4 (0.089 g; 71.6%) as a white solid. [M+H]=608.52.

$^1$H NMR (500 MHz, CD$_3$OD): δ 7.70 (d; J=8.14 Hz; 1H); 7.34 (t; J=7.78 Hz; 2H); 7.23 (d; J=8.07 Hz; 2H); 7.17 (t; J=7.39 Hz; 1H); 6.03 (s; 1H); 5.56 (d; J=8.14 Hz; 1H); 5.36 (d; J=7.32 Hz; 1H); 4.93-4.94 (m; 1H); 4.41 (dd; J=9.29; 5.73 Hz; 1H); 4.26-4.29 (m; 2H); 3.89 (dd; J=9.83; 6.95 Hz; 1H); 3.16 (s; 1H); 2.66-2.67 (m; 1H); 2.58 (s, 1H); 1.32 (d; J=7.12 Hz; 3H); 1.17-1.18 (m; 12H).

$^{13}$C NMR (126 MHz, CDCl$_3$): δ 175.7, 172.8, 172.6, 172.5, 163.0, 151.0, 150.6, 150.6, 139.8, 129.9, 129.7, 125.0, 119.9, 119.8, 102.2, 91.1, 80.7, 79.3, 78.3, 75.3, 74.5, 74.5, 69.3, 64.7, 50.3, 33.7, 31.6, 22.6, 21.7, 21.6, 21.0, 21.0, 18.9, 18.8, 14.1.

Isobutyryl chloride (0.027 mL; 0.260 mmol; 1.5 eq) was added, slowly, to a mixture of the phosphate 3 (0.093 g; 0.173 mmol), triethylamine (0.072 mL; 0.519 mmol) and DMAP (0.0025 g; 0.02 mmol) in THF (5 mL) and water (5 mL) while cooled in an ice bath After a period of 1 h., an additional portion of isobutyryl chloride (0.5 eq) was added. After stirring for an additional 15 min., the reaction was acidified to pH=6-7 with aqueous HCl and the organics extracted into EtOAc (×2). The combined organic phases were washed with water, washed with brine, dried (MgSO4) and the volatiles removed under reduced pressure. The residue was purified using silica gel column chromatography using 0 to 10% MeOH in dichloromethane as eluent. This provided the desired phosphate 5 (0.089 g; 85.0%) as a white solid. [M+H]=608.50.

$^1$H NMR (500 MHz, CDCl$_3$): δ 7.69 (d; J=8.21 Hz; 1H); 7.32 (t; J=7.68 Hz; 2H); 7.21 (d; J=8.00 Hz; 2H); 7.16 (t; J=7.29 Hz; 1H); 6.03 (s; 1H); 5.72 (d; J=8.20 Hz; 1H); 5.33-5.34 (m; 1H); 4.99-5.00 (m; 1H); 4.44-4.47 (m; 1H); 4.35-4.37 (m; 2H); 3.99-4.00 (m; 1H); 3.83 (t; J=10.33 Hz; 1H); 2.68-2.69 (m; 1H); 2.67 (s, 1H); 1.35 (d; J=7.02 Hz; 3H); 1.21-1.22 (m; 12H).

$^{13}$C NMR (126 MHz, CDCl$_3$): δ 175.7, 173.0, 163.0, 151.1, 150.8, 139.8, 129.9, 129.8, 125.1, 120.2, 120.2, 02.3, 91.2, 80.3, 79.3, 78.5, 77.2, 77.0, 76.4, 75.3, 74.7, 69.4, 64.9, 50.4, 33.8, 21.7, 21.6, 21.1, 19.0, 18.8.

Example 7

Preparation of Compound 5

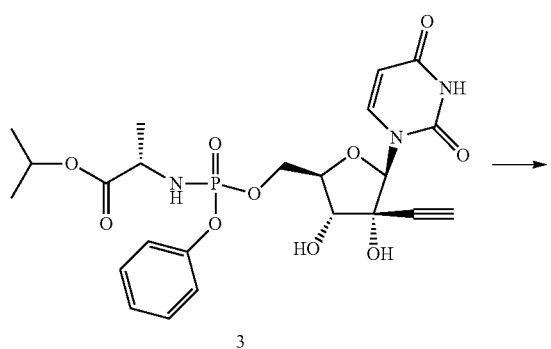

3

Example 8

Preparation of Compounds 6 and 7

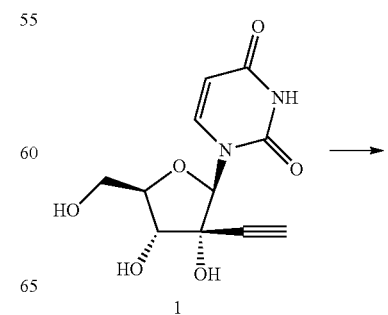

1

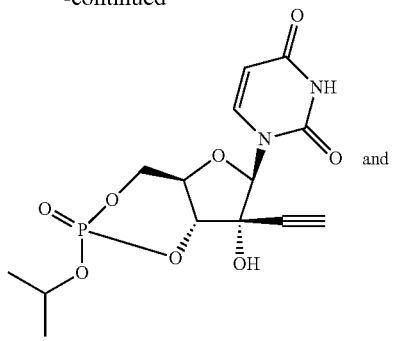

6; Isomer1

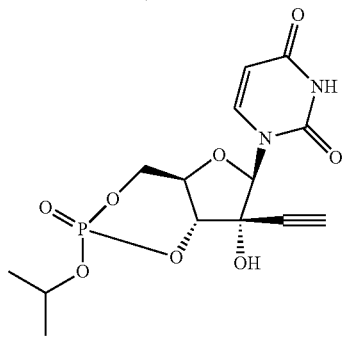

7; Isomer2

1-Isopropoxy-N,N,N',N'-tetraisopropylphosphinediamine (0.426 g; 1.465 mmol) was dissolved in anhydrous THF (3 mL) and added to the nucleoside 1 (0.300 g; 1.118 mmol) in anhydrous THF (2 mL) in a sealed tube. 5-(Ethylthio)-tetrazole (0.153 g; 1.174 mmol) was then added to the mixture and the tube was sealed and heated to 100 C (oil bath temp) for a period of 2.5 h. After cooling to room temperature, the tube was opened and tert-butyl hydroperoxide (11.2 mL of a 5.5M solution in isooctane; 61.5 mmol) was added and stirring was continued overnight. The volatiles were removed under reduced pressure and the residue purified using silica gel column chromatography using 0 to 10% MeOH in dichloromethane as eluent. Gave (i) Compound 6 (Isomer 1; 0.139 g; 33.4%) [M+H], 373.29, as a white solid followed by Compound 7 (Isomer 2; 0.039 g; 9.37%) [M+H], 373.29, also a white solid.

Example 9

Preparation of Compounds 15 and 16

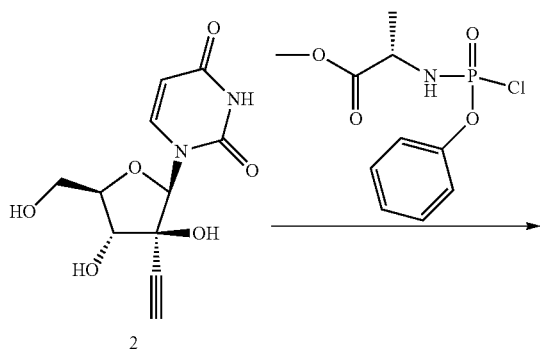

2

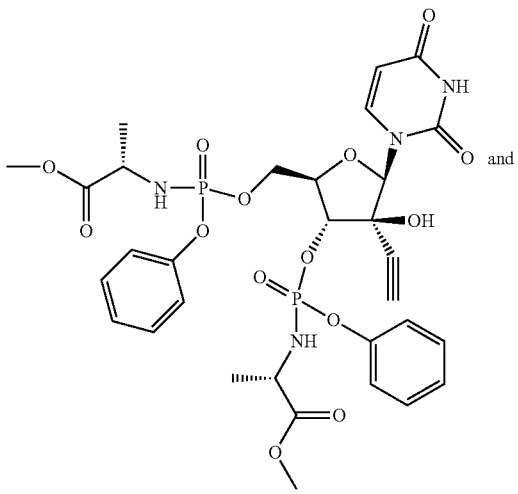

14

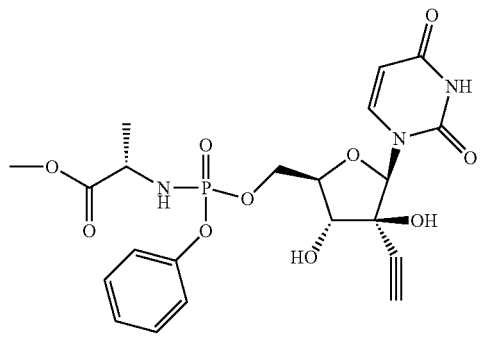

13

The phosphoryl chloride (0.0404 g; 0.145 mmol) was dissolved in anhydrous THF (1 mL) and added dropwise to a stirred mixture of N-methylimidazole (0.0288 g; 0.291 mmol) and nucleoside 2 (0.0130 g; 0.048 mmol) in anhydrous THF (1 mL) at 35 C. When the addition was complete the reaction mixture was stirred at this temperature for a further 1 h. The volatiles were removed under reduced pressure and the residue was purified using silica gel column chromatography using 0 to 2% MeOH in dichloromethane as eluent. Gave Compound 14 (0.0030 g; 8.25%) followed by Compound 13 (0.0070 g; 28.4).

Example 10

Preparation of Compound 17

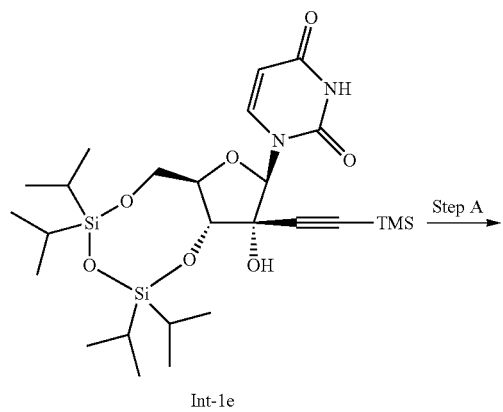

Int-1e

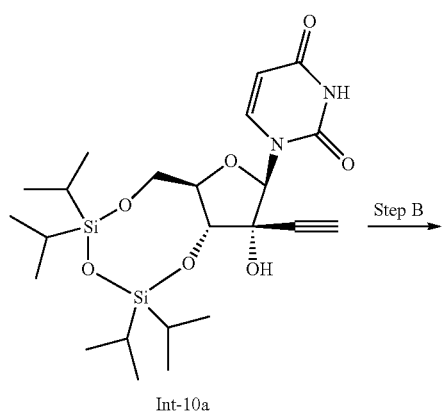

Int-10a

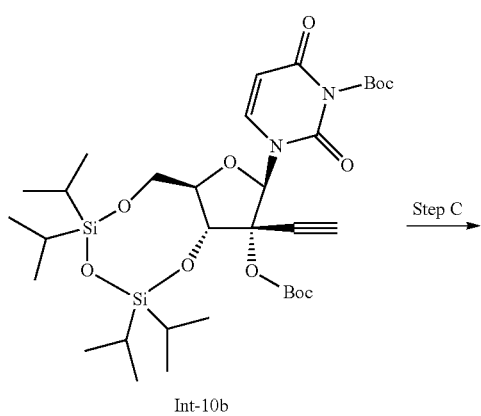

Int-10b

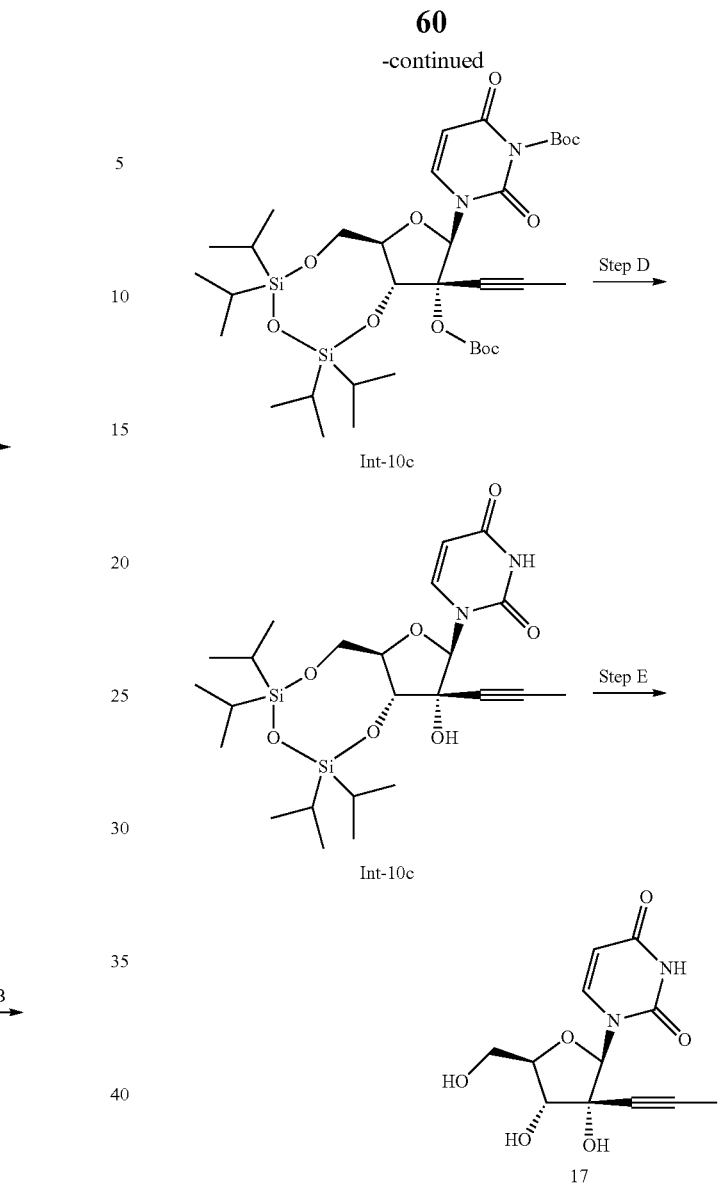

Step 10A—Synthesis of Compound Int-10a

The protected acetylene Int-1e (0.740 g; 1.269 mmol) was dissolved in methanol (4 mL) and potassium carbonate (0.307 g; 1.269 mmol) was added at room temperature. The resulting mixture was stirred for 10 min. The volatiles were removed under reduced pressure and the residue neutralized with 10% aqueous HCl and the organics were extracted into EtOAc. The organic layer was separated, dried (MgSO$_4$) and concentrated under reduced pressure. The residue was purified using silica gel column chromatography using 0 to 30% EtOAc in hexanes as eluent. This provided the desired Int-10a (0.176 g; 27.1%) as a white solid [M+H], 511.35.

Step 10B—Synthesis of Compound Int-10b

DMAP (0.178 g; 1.457 mmol) was added to a stirred mixture of the nucleoside 10a (0.372; 0.728 mmol), di-tert-butyl dicarbonate (0.477 g; 2.185 mmol) and triethylamine (0.381 mL; 2.185 mmol) in anhydrous dichloromethane (4 mL) at room temperature and the resulting mixture was stirred overnight. The reaction was partitioned between methylene chloride and 1N aq. HCl. The organic layer was separated, dried (MgSO$_4$) and the volatiles removed under reduced. The residue was purified using silica gel column chromatography using 0 to 10% EtOAc as eluent. This provided the desired product Int-10b (0.346 g; 66.8%). [M+H], 711.55.

Step 10C—Synthesis of Compound Int-10c n-Butyllithium (0.669 mL of a 1.6M solution in hexanes; 1.071 mmol) was added to a solution of Int-10b (0.346 g; 0.487 mmol) in anhydrous THF (4 mL) at −78 C, under an atmosphere of nitrogen. The resulting mixture was stirred for 30 min and HMPA (0.249 mL; 1.431 mmol) and methyl iodide (0.039 g; 0.633 mmol) were added. After stirring for a further 2 h., sat. aq. ammonium chloride was added. The organics were extracted into EtOAc. The organic phase was separated, dried (MgSO4) and the volatiles removed under reduced pressure. The residue was purified using silica gel column chromatography using 0 to 10% EtOAc in hexanes aseluent. This provided the desired alkylated product Int-10c (0.100 g; 28.3%). [M+H], 725.59.

Step 10D—Synthesis of Compound Int-10d

A mixture of trifluoroacetic acid (0.4 mL) in dichloromethane (2 mL) was added to the carbonate Int-10c and the resulting reaction was stirred at room temperature for 2 h. The volatiles were removed under reduced pressure and the residue was partitioned between EtOAc and sat. aq. sodium bicarbonate. The organic phase was separated, dried (MgSO4) and the concentrated. The crude product was purified using silica gel column chromatography using 0 to 30% EtOAc in hexanes as eluent. This provided the desired deprotected product Int-10d (0.060 g; 83%). [M+H], 525.48.

Step 10E—Synthesis of Compound 17

A solution of TBAF (0.229 mL of a 1.0M in THF; 0.229 mmol) was added to a solution of the silyl ether Int-10d (0.060 g; 0.114 mmol) in THF (2 mL). The resulting mixture was stirred for 45 min., then concentrated under reduced pressure. The crude product was purified using silica gel column chromatography using 0 to 10% MeOH in dichloromethane as eluent. This provided the desired nucleoside 17 (0.023 g; 71.3%). [M+H], 283.22.

$^1$H NMR δ (ppm)(CH$_3$OH-d$_4$): 1.77 (3H, s), 3.36 (1H, s), 3.76 (1H, dd, J=12.52, 2.99 Hz), 3.88 (1H, dt, J=8.93, 2.64 Hz), 3.98 (1H, dd, J=12.52, 2.36 Hz), 4.13 (1H, d, J=8.93 Hz), 5.71 (1H, d, J=8.11 Hz), 6.02 (1H, s), 8.05 (1H, d, J=8.11 Hz).

Example 11

Preparation of Compound 29

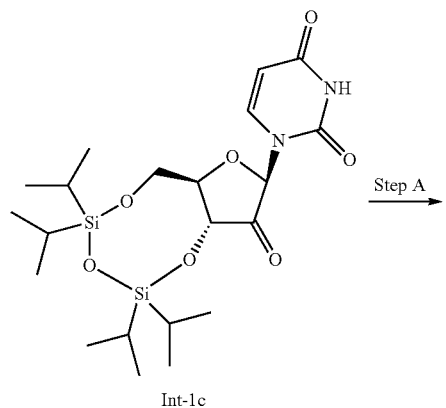

Int-1c

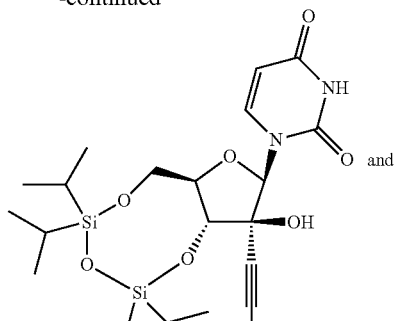

Int-11a

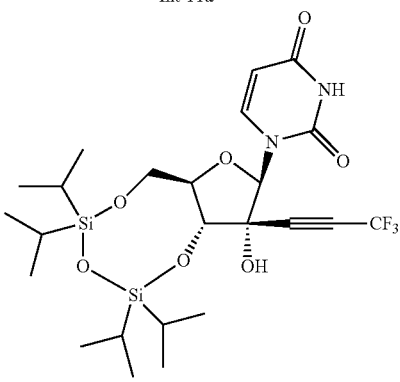

Int-11b

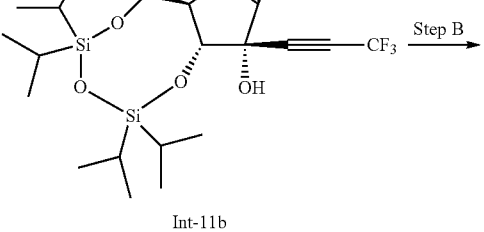

Int-11b

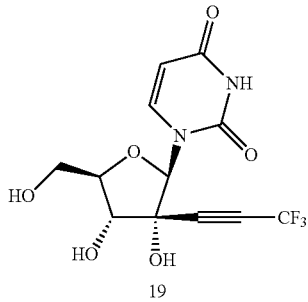 [SMILES: O=c1ccn([C@@H]2O[C@H](CO)[C@@H](O)[C@]2(O)C#CC(F)(F)F)c(=O)[nH]1]

19

Step 11A—Synthesis of Compounds Int-11a anf Int-11b

N-Butyllithium (11.61 mL of a 1.6M solution in hexanes; 18.57 mmol) was added to anhydrous THF (50 mL) and the resulting mixture was cooled to −78 C, under an atmosphere of nitrogen. Trifluoromethylacetylene gas was bubbled through the solution for 5 min and stirring was continued for 15 min. The ketone Int-1c (3.00 g; 6.19 mmol) in anhydrous THF (4 mL) was added and stirring was continued for a further 1 h. The reaction was quenched with sat. aq ammonium chloride. After warming to room temperature and the organics extracted into EtOAc. The organic phase was separated, dried (MgSO4) and the volatiles removed under reduced pressure. The residue was purified using silica gel column chromatography using 0 to 30% EtOAc in hexanes to give (i) Int-11a (0.605 g; 18.15%) [M+H], 551.57, followed by (ii) Int-11b (0.110 g; 3.07%), [M+H], 551.57.

Step 11B—Synthesis of Compound 19

TBAF (0.45 mL of a 1.0M solution in THF; 0.45 mmol) was added to a stirred solution of the silyl ether Int-11b (0.130 g; 0.225 mmol) in THF (3 mL). The resulting mixture was stirred for 1 h., then the volatiles were removed under reduced pressure. The residue was purified using silica gel column chromatography using 0 to 10% MeOH in dichloromethane as eluent. This provided the desired triol 19 (0.012 g; 15.89%). [M+H], 309.31.

Example 12

Preparation of Compound 26

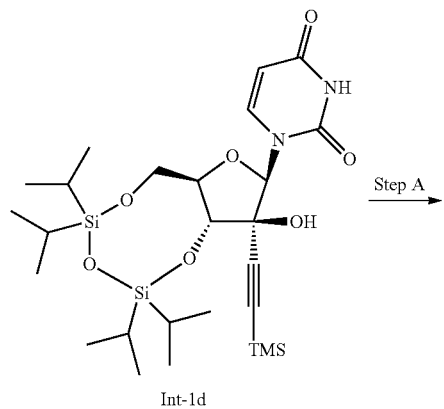

Int-1d

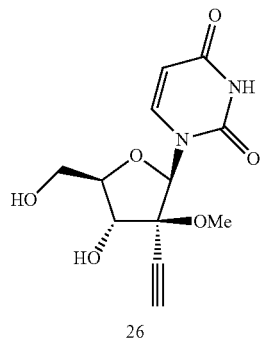

26

Step 12A—Synthesis of Compound Int-12a

LiHMDS (0.515 mL of a 1.0M solution in toluene; 0.515 mmol) was added to a solution of the alcohol Int-1d (0.100 g; 0.172 mmol) in anhydrous THF (5 mL) at −78 C, under an atmosphere of nitrogen. After stirring at this temperature for 1 h., the reaction mixture was allowed to warm to room temperature. Saturated aq ammonium chloride was added and the organics were extracted into EtOAc. The organic phase was separated, dried (MgSO4) and the volatiles removed under reduced pressure. The residue was purified using silica gel column chromatography. This provided the methyl ether Int-12a (0.045 g; 43.9%). [M+H], 525.36

Step 12B—Synthesis of Compound 26

TBAF (0.201 mL of a 1.0M in THF; 0.201 mmol) was added to the methyl ether Int-12a (0.040 g; 0.067 mmol) in THF (3 mL) at room temperature. After stirring for 1 h., the volatiles were removed under reduced pressure and the residue purified using silica gel column chromatography using 0 to 10% MeOH in dichloromethane as eluent. This provided the diol 26 (0.0112 g; 59.2%). [M+H], 283.29.

$^1$H NMR δ (ppm)(CH$_3$OH-d$_4$): 3.43 (3H, s), 3.78 (2H, m), 3.85 (2H, m), 4.17 (1H, d, J=6.14 Hz), 5.67 (1H, d, J=8.18 Hz), 6.36 (1H, s), 7.84 (1H, d, J=8.18 Hz).

Example 13

Preparation of Compound 29

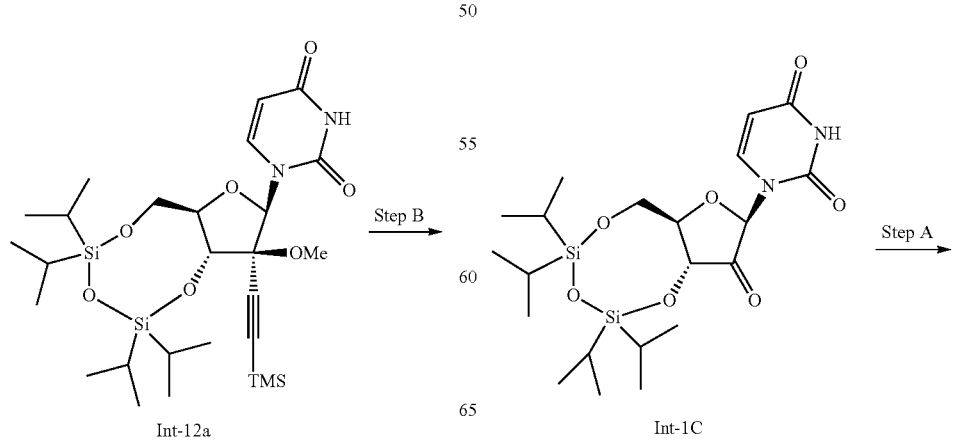

Int-12a   Int-1C

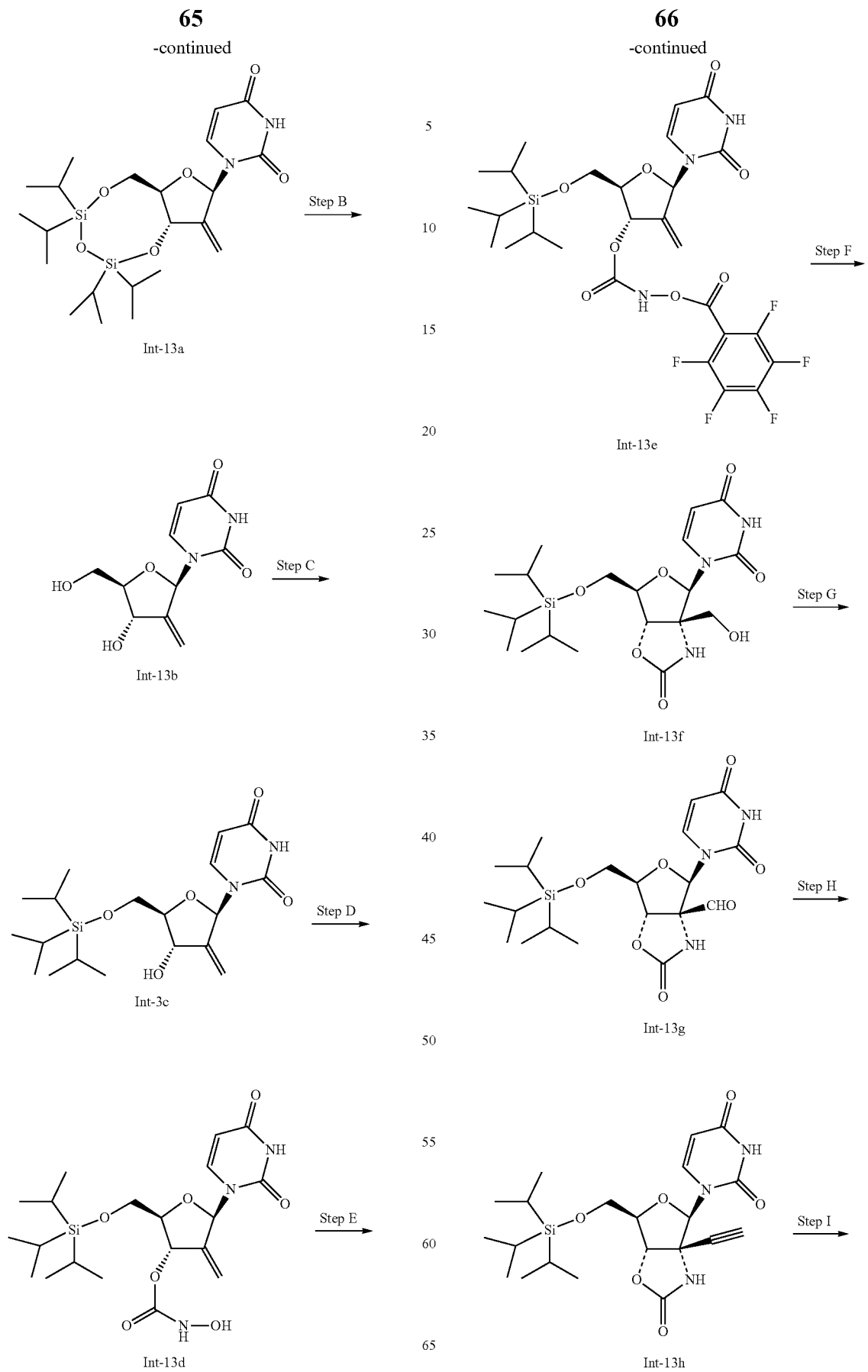

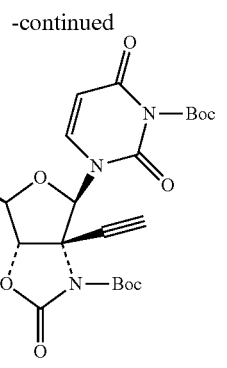

Int-13i

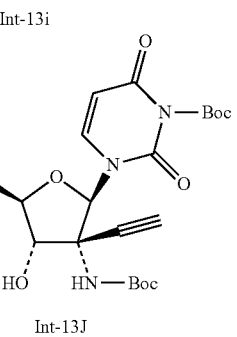

Int-13J

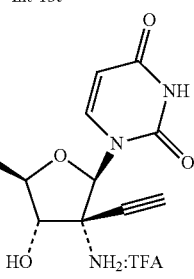

Int-13k

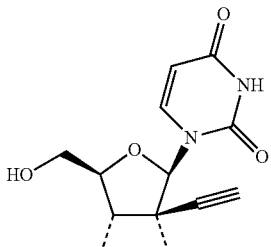

29

Step 13A—Synthesis of Compound Int-13a

Methyltriphenylphosphonium bromide (16.85 g; 47.2 mmol) was suspended in anhydrous THF (160 mL) and cooled in an ice bath under an atmosphere of nitrogen. A solution of potassium hexamethyldisilazide (90 mL of a 0.5M solution in toluene; 45 mmol) was added dropwise to the suspension. The resulting orange suspension was stirred for 0.5 h., then a solution of the ketone Int-1c (6.0 g; 12.38 mmol) in anhydrous THF (60 mL) was added. The reaction mixture was kept in the refridgerator overnight, then at room temperature for 3 h. The reaction was quenched with sat. aq. ammonium chloride and the organics extracted into EtOAc. The organic phase was separated, washed with brine, dried (MgSO4) and the volatiles removed under reduced pressure. The residue was purified using silica gel column chromatography twice using 0 to 30% EtOAc in hexanes as eluent. This provided the alkene Int-13a (2.61 g; 43.7%) as a white solid. [M+H]=483.19

Step 13B—Synthesis of Compound Int-13b

TBAF (20.72 mL of a 1.0M solution in toluene; 20.72 mmol) was added to a solution of the silyl ether Int-14a (5.00 g; 10.36 mmol) in anhydrous THF (20 mL) at room temperature and the resulting mixture was stirred at room temperature for 1 h. The volatiles were removed under reduced pressure. The residue was purified using silica gel column chromatography twice using 5 to 10% MeOH in dichloromethane as eluent. This provided the methyl ether Int-13b (2.16 g; 87%).

Step 13C—Synthesis of Compound Int-13c

Triisopropylsilyl trifluoromethanesulfonate (2.417 mL; 8.99 mmol) and 2,6-lutidine (1.257 mL; 10.79 mmol) were added to a solution of the diol Int-13b (2.16 g; 8.99 mmol) in anhydrous dichloromethane (20 mL) while cooled in an ice bath and the resulting mixture was stirred and warmed room temperature, overnight. The volatiles were removed under reduced pressure. The residue was purified using silica gel column chromatography twice using 0 to 10% MeOH in dichloromethane as eluent. This provided the methyl ether Int-13c (1.27 g; 65%), containing some of the sec-silyl ether. [M+H], 397.47.

Step 13D—Synthesis of Compound Int-13d

Carbonyldiimidazole (0.88 g; 5.44 mmol) was added, in one portion, to a stirred solution of the alcohol Int-13c (1.35 g; 2.72 mmol) in anhydrous dichloromethane (20 mL). The resulting mixture was stirred at room temperature for 2.5 hours. Satured NH4Cl was added to the reaction mixture and the organic layer was separated and dried with Na2SO4. The solvent was removed under reduced pressure to obtain a white solid reaction adduct. This adduct was added pyridine (20 mL) and then hydroxylamine hydrochloride (0.94 g, 13.59 mmol) was added and the resulting reaction mixture was stirred at room temperature for 1 hour. Pyridine was removed under reduced pressure. The residue was purified using silica gel column chromatography using 0 to 10% MeOH in dichloromethane as eluent. This provided the methyl ether Int-13d (0.965 g). [M+H], 456.45.

Step E—Synthesis of Compound Int-13e

Pentafluorobenzoyl chloride (0.315 g; 1.364 mmol) was dissolved in dichloromethane (2 mL) and added dropwise to a stirred mixture of the N-hydroxycarbamate Int-13d (0.518 g; 1.137 mmol) and triethylamine (0.238 mL; 1.71 mmol) in anhydrous dichloromethane (18 mL) while cooled in an ice bath. The resulting mixture was stirred for 1 h., then partitioned between EtOAc and 10% aq. HCl. The organic phase was separated, washed with sat. aq. sodium bicarbonate, brine, dried (MgSO4) and the volatiles removed under reduced pressure. The residue was purified using silica gel column chromatography using 0 to 100% EtOAc in hexanes as eluent. This provided the desired ester Int-13e (0.720 g; 97%) as a white solid. [M+H], 650.57.

Step 13F—Synthesis of Compound Int-13f

Potassium osmate (0.0204 g; 0.06 mmol) in water (1 mL) was added dropwise to the pentafluorophenyl ester Int-13e (0.720 g; 1.11 mmol) in tert-butanol (24 mL) and water (8 mL) and the resulting mixture was stirred overnight at room temperature. The reaction was quenched with sodium sulfite (200 mg). The suspension was filtered and the filtrate concentrated under reduced pressure. Dichloromethane was added to the residue and dried with MgSO4. The solids were removed by filtration and the volatiles removed under reduced pressure. The crude product was purified using silica gel column chromatography using 0 to 5% MeOH in dichloromethane as eluent. This provided the desired cyclic carbamate Int-13f (0.321 g; 63.3%) as a white solid. [M+H]=456.45

Step 13G—Synthesis of Compound Int-13g

Dess-martin periodinane (0.598 g; 1.41 mmol) was added, in one portion, to a stirred solution of the alcohol Int-13f (0.321 g; 0.705 mmol) in dichloromethane (10 mL) and the resulting mixture was stirred at room temperature for 1 h. The reaction mixture was partitioned between EtOAc and 10% aq. sodium thiosulfate. The organic phase was separated, washed with sat aq. sodium bicarbonate, dried and the volatiles removed under reduced pressure. The crude product Int-13g (0.320 g) was used without purification. [M+H], 454.44

Step 13H—Synthesis of Compound Int-13h

Potassium carbonate (0.195 g; 1.41 mmol) was added, in one portion, to a stirred mixture of the crude aldehyde Int-13g (0.321 g; 0.705 mmol) and Ohira-Bestmann reagent (0.203 g; 1.06 mmol) in methanol (5 mL) and the resulting mixture was stirred at room temperature overnight. A further portion of the Ohira-Bestmann reagent (0.102 g) was added and stirring was continued for a further 1.5 h. and the volatiles were removed under reduced pressure. The crude product was purified using silica gel column chromatography using 0 to 10% MeOH in dichloromethane as eluent. This provided the alkyne Int-13h (0.167 g; 52.7%). [M+H], 450.44.

Step 13I—Synthesis of Compound Int-13i

DMAP (0.136 g; 1.11 mmol) was added, in one portion, to a stirred mixture of the cyclic carbamate Int-13h (0.167 g; 0.371 mmol) and di-tert-butyl dicarbonate (0.243 g; 1.11 mmol) in dichloromethane (3 mL) and the resulting mixture was stirred at room temperature overnight. Further portions of the DMAP (0.100 g) and di-tert-butyl dicarbonate (0.100 g) were added and stirring was continued for a further 1.0 h. and the volatiles were removed under reduced pressure. The crude product was purified using silica gel column chromatography using 0 to 50% EtOAc in hexanes as eluent. This provided the carbamate Int-13i (0.165 g; 68.4%) as a white solid.

Step 13J—Synthesis of Compound Int-13j

Cesium carbonate (0.017 g; 0.2 mmol) was added, in one portion, to a stirred solution of the cyclic carbamate Int-13i (0.165 g; 0.254 mmol) in methanol (4 mL) and the resulting mixture was stirred at room temperature for 2 h. The volatiles were removed under reduced pressure. The crude product was purified using silica gel column chromatography using 0 to 50% EtOAc in hexanes as eluent. This provided the carbamate Int-13j (0.131 g; 83%) as a white solid. [M+H], 624.66.

Step 13K—Synthesis of Compound Int-13k

A mixture of dichloromethane (4 mL) and trifluoroacetic acid (0.8 mL) was added to the carbamate Int-13j (0.131 g; 0.21 mmol) while cooled in an ice bath. The resulting mixture was allowed to stand at room temperature for 1 h. The volatiles were removed under reduced pressure. Dichloromethane was added to the residue reconcentrated and repeated. Finally, an additional portion of dichloromethane was added followed by triethylamine After concentration, the residue was purified using silica gel column chromatography using 0 to 5% MeOH in dichloromethane as eluent. This provided the silylether Int-13k (0.074 g; 83%) as a white solid. [M+H]=424.46.

Step 13L—Synthesis of Compound 29

TBAF (0.19 mL of a 1M solution in THF; 0.19 mmol) was added a solution of the silyl ether Int-13k (0.074 g; 0.17 mmol) in THF (2 mL). The resulting mixture was allowed to stand at room temperature for 0.5 h. and the volatiles were removed under reduced pressure. The residue was twice purified using silica gel column chromatography using 0 to 15% MeOH in dichloromethane as eluent. This provided the nucleoside 29 (0.042 g; 90%) as a white solid.

$^1$H NMR (599 MHz, CD$_3$OD): δ 8.10 (d; J=8.12 Hz; 1H); 5.90 (s; 1H); 5.67 (d; J=8.11 Hz; 1H); 4.26 (d; J=8.22 Hz; 1H); 3.93-3.94 (m; 2H); 3.75 (dd; J=12.32; 2.93 Hz; 1H); 3.22 (t; J=8.46 Hz; 1H); 2.92 (s; 1H).

$^{13}$C NMR (151 MHz, CD$_3$OD): δ 166.2, 152.7, 143.9, 142.5, 136.1, 120.9, 108.7, 102.2, 92.7, 84.8, 84.4, 75.9, 75.6, 61.8, 61.8, 60.7, 59.6, 59.6, 59.6, 50.9, 50.4, 50.4, 50.3, 24.9, 20.9, 20.8, 20.8, 14.1.

Example 14

Preparation 5'-Triphosphates

The preparation of the triphosphates disclosed were carried under contractual agreement with TriLink biotechnologies, San Diego, Calif. or carried out as set forth for the conversion of Int-14a to Int-14b.

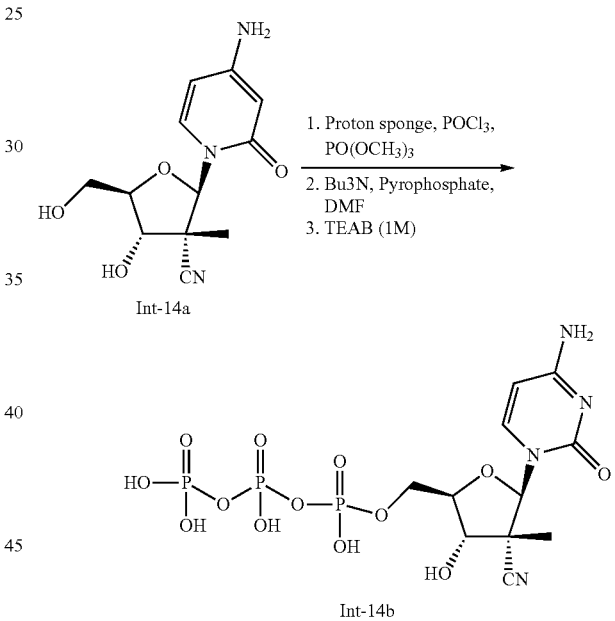

A solution of 1-[(2R,3R,4S,5R)-3-cyano-4-hydroxy-5-(hydroxymethyl)-3-methyloxolan-2-yl]-1,2,3,4-tetrahydropyrimidine-2,4-dione (Int-14a, 15 mg, 0.05 mmol, 1.00 equiv) in trimethylphosphate (1.0 mL) was placed under nitrogen atmosphere. To this solution was added proton sponge (17 mg, 0.08 mmol, 1.50 equiv) and the resulting reaction was cooled to 0° C. To the cooled solution was added phosphoryl trichloride (32 mg, 0.21 mmol, 4.50 equiv) and the resulting reaction was allowed to stir for 4 hours at 0° C. Pyrophosphate (200 mg, 0.37 mmol, 5.00 equiv), N,N-dimethylformamide (1.0 mL) and tributylamine (0.03 mL, 10.00 equiv) were then added to the reaction mixture and the resulting reaction was allowed to stir for an additional 1 hour at 0° C. The reaction was then quenched by the addition of 3.0 mL of triethylammonium bicarbonate buffer (1M) and the resulting solution was concentrated in vacuo. The residue obtained was purified using Prep-HPLC as follows: (1#-Pre-HPLC-001(SHIMADZU)): Column, 1#-PrepC-008(Atlantis HILIC Silica 19*150 186003959 0110182551 kk 03), mobile phase: acetonitrile and water with 50 mmol ammonium bicarbonate; Detector, UV 220 & 254 nm This provided 0.7 mg of compound Int-14b as a light yellow solid.
$^1$H-NMR (400 MHz, D$_2$O): δ 7.96 (d, 1H), 6.45 (s, 1H), 6.16 (d, 1H), 4.39 (m, 1H), 4.31 (m, 2H), 4.28 (m, 1H), 1.31 (s, 3H).
$^{31}$P-NMR (162 MHz, D$_2$O): δ −10.01 (d, 1P), −10.62 (d, 1P), −22.28 (t, 1P) MS (ESI) m/z 506.7 [M]
Exemplified by:
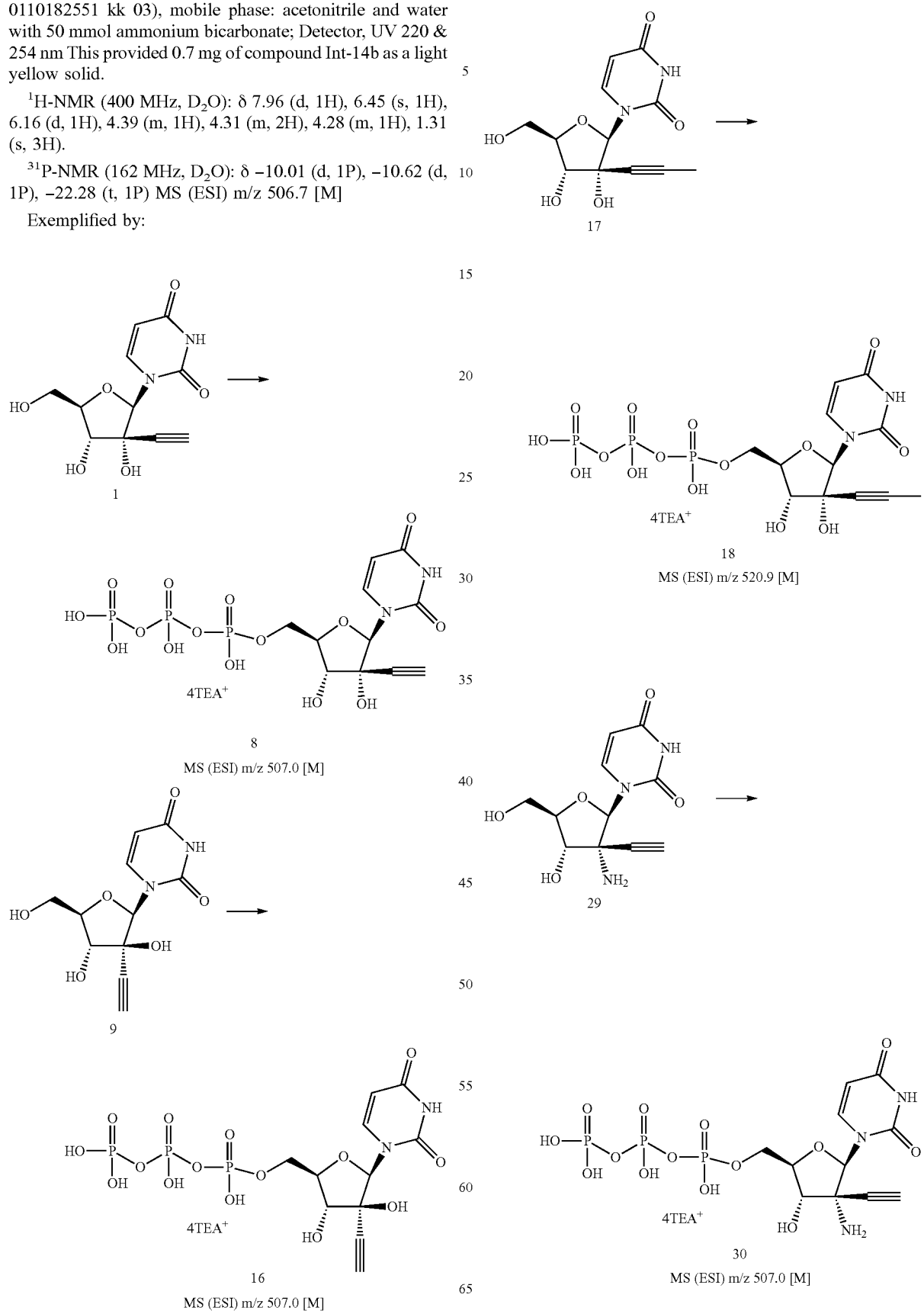

Example 15

Preparation of Compound 31

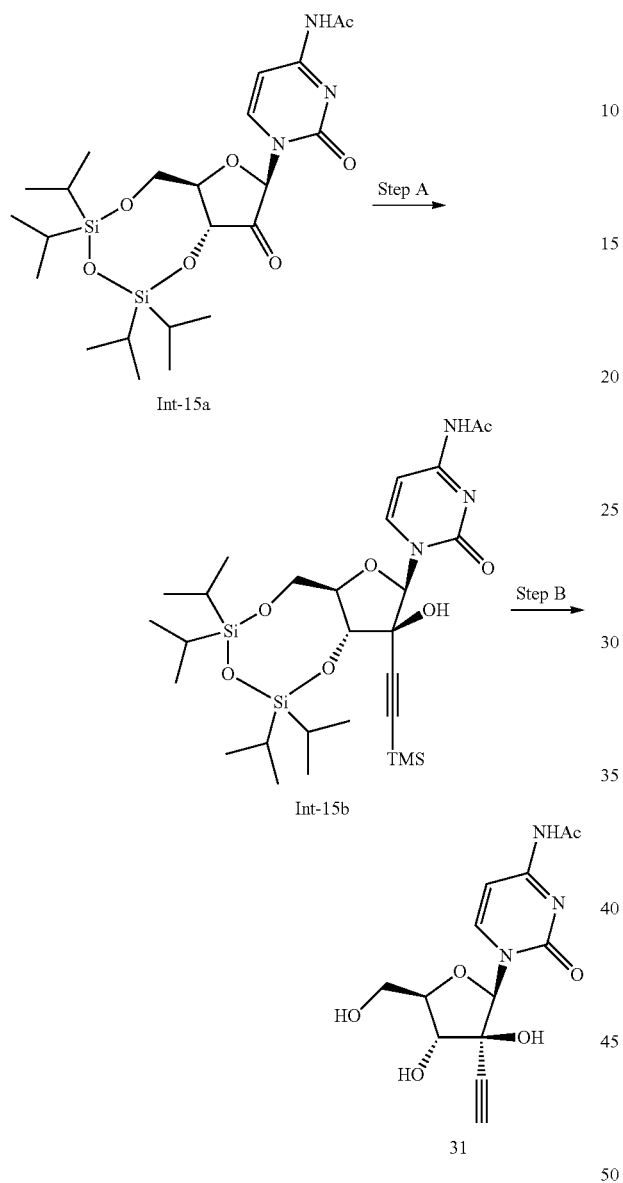

Step 15A—Synthesis of Compound Int-15b nBuLi (0.285 mmol; a 1.6M solution in hexanes) was added dropwise to a stirred solution of the acetylene (0.028 g; 0.285 mmol) in anhydrous THF (1 mL) at −78 C, inder an atmosphere of nitrogen. When the addition was complete, the ketone Int-15a (0.150 g; 0.285 mmol) in anhydrous THF (1 mL) was added. After stirring for a further 1 h., the reaction was quenched with sat aq. ammonium chloride. The organics were extracted into EtOAc, separated, dried and the volatiles removed under reduced pressure. The residue was purified using silica gel column chromatography using EtOAc in hexanes (1:1) as eluent. This provided the desired addition product Int-15b (0.040 g) containing another component. [M+H], 624.2.

Step 15B—Synthesis of Compound 31

TBAF (0.071 mL of a 1.0M solution in THF was added to the silyl ether Int-15B (0.022 g; 0.035 mmol) in THF (1 mL) and the resulting mixture was stirred for 1 h. The volatiles were removed under reduced pressure and the residue purified using silica gel column chromatography using 10% MeOH in dichloromethane as eluent. This provided the desired nucleoside analogue 31 (0.002 g; 18.3%).

$^1$H NMR δ (ppm)(CH$_3$OH-d$_6$): 2.10 (3H, s), 3.34 (1H, s), 3.59-3.65 (2H, m), 3.80 (1H, d, J=5.16 Hz), 3.87 (1H, t, J=5.27 Hz), 5.11 (1H, t, J=5.34 Hz), 5.69 (1H, d, J=5.69 Hz), 6.27 (1H, s), 6.35 (1H, s), 7.15 (1H, d, J=7.56 Hz), 8.09 (1H, d, J=7.57 Hz), 10.86 (1H, s)

Example 16

Preparation of Compound 32

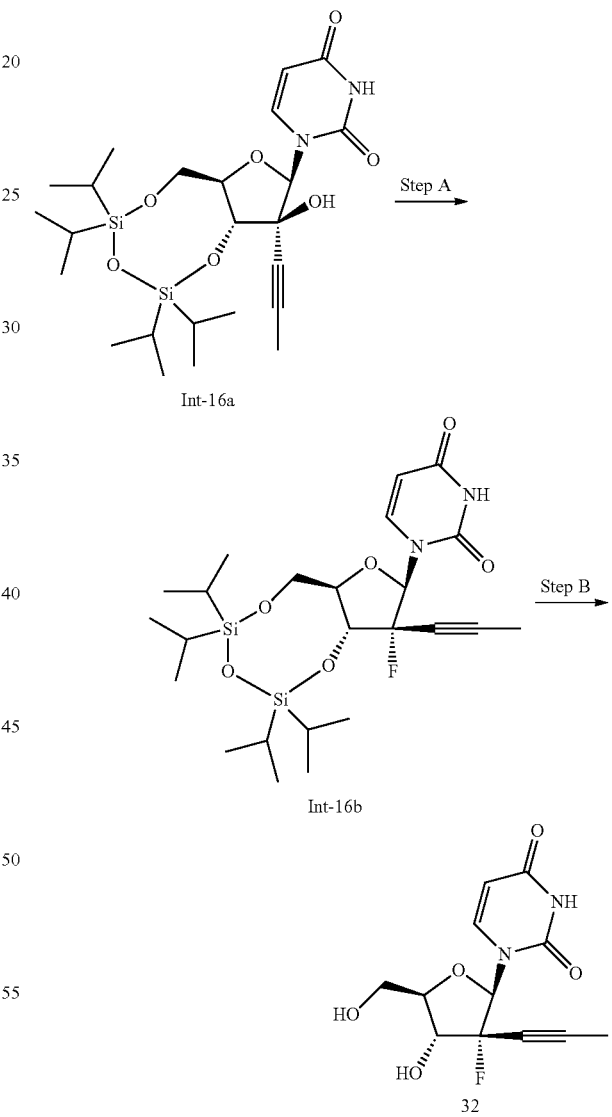

Step 16A—Synthesis of Compound Int-16b

DAST (0.698 mL; 5.33) was added dropwise to a stirred solution of the acetylene Int-16a (0.466 g; 0.888 mmol) in anhydrous toluene (1 mL) at −20 C, under an atmosphere of nitrogen. After stirring for a further 45 min., the reaction was quenched with sat aq. sodium bicarbonate. The organics were extracted into EtOAc, separated, dried and the volatiles removed under reduced pressure. The residue was purified using silica gel column chromatography using EtOAc in hexanes (1:4) as eluent. This provided the desired addition product Int-16b (0.106 g; 22.7%). [M+H], 527.37.

Step 16B—Synthesis of Compound 32

TBAF (0.668 mL of a 1M solution in THF; 0.688 mmol) was added dropwise to a stirred solution of the acetylene Int-16a (0.177 g; 0.344 mmol) in THF (2 mL). After stirring at room temperature for a 45 min., the reaction was concentrated under reduced pressure. The residue was purified using silica gel column chromatography using MeOH in dichloromethane (1:10) as eluent. This provided the desired product 32 (0.060 g; 63.2%). [M+H], 285.19.

$^1$H NMR δ (ppm)(CH$_3$OH-d$_4$): 1.86 (3H, d, J=6.22 Hz), 3.33 (1H, t, J=2.06 Hz), 3.80 (1H, dd, J=12.67, 2.71 Hz), 3.95 (1H, d, J=9.66 Hz), 3.99 (1H, dd, J=12.68, 2.17 Hz), 4.24 (1H, dd, J=20.26, 9.41 Hz), 5.73 (1H, d, J=8.12 Hz), 6.20 (1H, d, J=17.23 Hz), 7.97 (1H, d, J=8.13 Hz).

Example 17

Inhibition of HCV NS5B Polymerase by Nucleoside Triphosphate Analogs

To measure inhibition of the enzymatic activity of the HCV NS5B RNA-dependent RNA polymerase by the nucleoside triphosphate compounds of the present invention, a radiolabeled nucleotide incorporation assay was used. This assay is a modified version of the assay described in International Publication No. WO2002/057287. Briefly, 50 µL reactions containing 20 mM HEPES (pH 7.3); 7.5 mM DTT; 20 units/mL RNasIN; 1 µM each of ATP, GTP, UTP and CTP; 20 µCi/mL [$^{33}$P]-CTP; 10 mM MgCl; 60 mM NaCl; 100 µg/mL BSA; 0.021 µM DCoH heteropolymer RNA template; and 5 nM NS5B (1b-BKΔ55) enzyme are incubated at room temperature for 1 hour. The assay is then terminated by the addition of 500 mM EDTA (50 µL). The reaction mixture is transferred to a Millipore DE81 filter plate and the incorporation of labeled CTP is determined using Packard TopCount. Compound IC$_{50}$ values can then be calculated from experiments with 10 serial 3-fold dilutions of the inhibitor in duplicate. The intrinsic potency (Ki) of an NTP inhibitor is derived from its NS5B IC$_{50}$ using the Cheng-Prusoff equation for a competitive inhibitor, as described in Cheng et al., *Biochem Pharmacol* 22:3099-3108 (1973): Ki=IC$_{50}$/(1+[S]/K$_m$), where [S]=1 µM, and K$_m$ is the concentration of cognate NTP yielding half-maximal enzyme activity in the assay absent exogenous inhibitors.

Data was obtained using this method for the NTP analogs of selected compounds below of the present invention, and is set forth below. This data indicates that the nucleoside triphosphate (NTP) of the compounds are potent and effective inhibitors of HCV NS5B polymerase.

| Compound | NTP Ki (µM) |
|---|---|
| 8 | 0.036 |
| 16 | ~19 |
| 18 | 0.058 |
| 25 | ~12 |
| 30 | 1.2 |

The compounds in the above table are triethylamine salts of the nucleoside triphoshphate derivatives of various mucleoside compounds of the present invention.

Example 18

Replicon Activity and Cytotoxicity Assays

To measure cell-based anti-HCV activity of the compounds of the present invention, replicon cells (1b-Con1) are seeded at 5000 cells/well in 96-well plates one day prior to treatment with a compound of the invention. Various concentrations of a test compound of the invention in DMSO are then added to the replicon cells, with the final concentration of DMSO at 0.5% and fetal bovine serum at 10% in the assay media. Cells are harvested three days post-dosing and the replicon RNA level is determined using real-time RT-PCR (Taqman assay) with GAPDH RNA as endogenous control. EC$_{50}$ values are calculated from experiments with 10 serial twofold dilutions of the inhibitor in triplicate. To measure cytotoxicity in replicon cells of an inhibitor, an MTS assay is performed according to the manufacturer's protocol for CellTiter 96 Aqueous One Solution Cell Proliferation Assay (Promega, Cat #G3580) three days post dosing on cells treated identically as in replicon activity assays. $CC_{50}$ is the concentration of inhibitor that yields 50% inhibition compared to vehicle-treated cells. Cytotoxicity in other types of cells can be measured using the same MTS protocol.

Data was obtained using this method for selected compounds of the present invention, and is set forth below. This data indicates that the compound possesses significant cytotoxicity windows over replicon activity.

| Compound | Replicon (1b) $EC_{50}$ (μM) | Cytotoxicity (μM) |
|---|---|---|
| 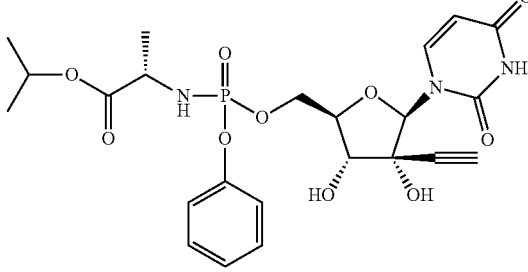<br>Isomer 1<br>2 | 0.09 | >100 |
| 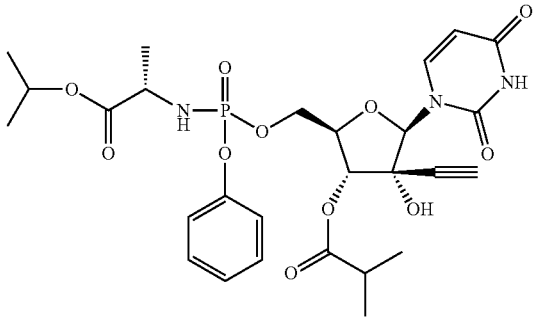<br>Isomer 1<br>4 | 0.10 | >100 |
| 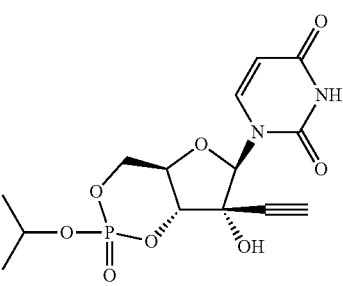<br>Isomer 1<br>6 | 21 | >100 |

-continued

| Compound | Replicon (1b) EC$_{50}$ (μM) | Cytotoxicity (μM) |
|---|---|---|
| 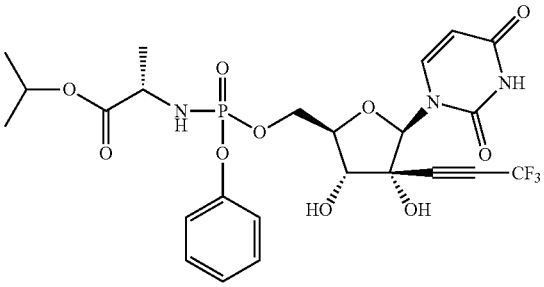 20 | 25.2 | 40.7 |
| 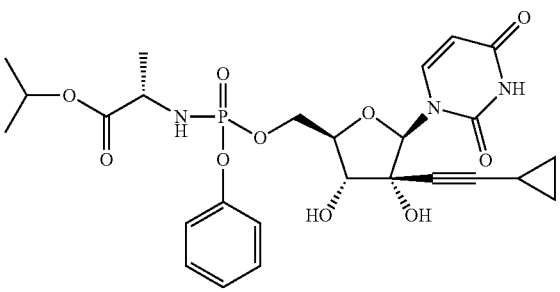 21 | 1.1 | 14.2 |
| 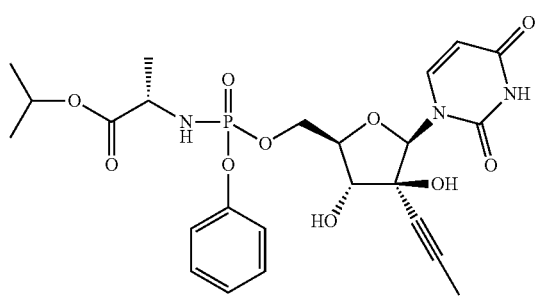 Isomer 1 23 | 0.94 | >100 |
| 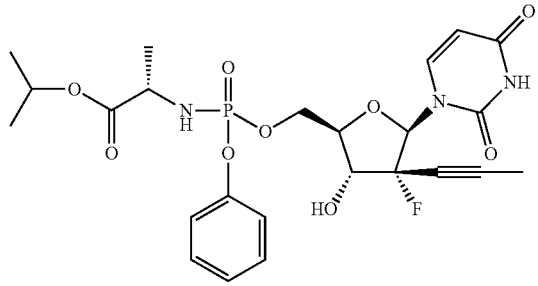 41 | 45.7 | 74.4 |

Example 19

Mitochondrial Toxicity Assay

Mitochondrial toxicity in replicon cells of an inhibitor can be evaluated by its effect on the mitochondrial genome copy number relative to a nuclear gene control. Replicon cells are seeded at 60,000 cells/well in 6-well plates one day prior to inhibitor treatment. Various concentrations of an inhibitor in culture medium are added on the first day of treatment and dosing media are refreshed every three days thereafter. Cells are harvested at the indicated days post dosing; the total DNA is isolated using DNeasy Blood & Tissue Kit (Qiagen, Cat #69504) and quantitated by standard spectrophotometric methods. Two alternative sets of mitochondrial-specific DNA primer can be used: 1) 5'-CACCCAAGAACA-GGGTTTGT-3' (SEQ. ID. NO. 1) (F3212, forward), 5'-TG-GCCATGGGTATGTTGTTAA-3' (SEQ. ID. NO. 2) (R3319, reverse), 6-FAM-5'-TTACCGGGCTCTGC-CATCT-3'-TAMRA (SEQ. ID. NO. 3) (probe) (see Bai et al., Ann NY Acad Sci 1011:304-309 (2004)); or 2) 5'-TGC-CCGCCATCATCCTA-3' (SEQ. ID. NO. 4) (COX II, forward), 5'-CGTCTGTTATGTAAAGGATGCGT-3' (SEQ. ID. NO. 5) (COX II, reverse), 6-FAM-5'-TCCTCATCGC-CCTCCCATCCC-3'-TAMRA (SEQ. ID. NO. 6) (probe) (see Stuyver et al., Antimicrob Agents Chemother 46:3854-3860 (2002)). Primers are used at 500 nM and probes at 200 nM in the Taqman quantitative PCR assay. The nuclear gene control quantitation is run in parallel for 18S DNA using ABI PDAR part #4310875 (20×). The ΔCT value (CT difference between mt DNA and 18S DNA) from inhibitor-treated cells is compared to that of vehicle-treated cells. Mitochondrial toxicity in other types of cells can be measured using the same protocol.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the structure:

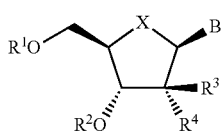
(I)

or a pharmaceutically acceptable salt thereof, wherein:

B is a pyrimidine base;
X is O, S or $CH_2$;
$R^1$ is H,

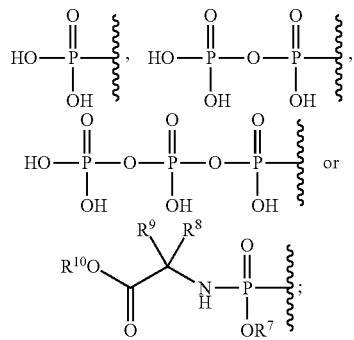

$R^2$ is H, —C(O)—($C_1$-$C_6$ alkyl) or

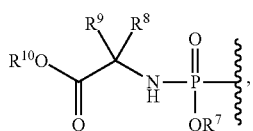

or $R^1$ and $R^2$ join to form a group having the formula:

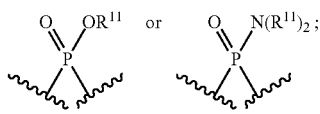

$R^3$ is H, F, —$OR^{12}$, $NH_2$, —CN, $N_3$, —$SR^{12}$ or —C≡$CR^5$;

$R^4$ is F, —$OR^{12}$, $NH_2$, —CN, $N_3$, —$SR^{12}$, —O—($C_6$-$C_{10}$ aryl) or —C≡$CR^5$, such that at least one of $R^3$ and $R^4$ must be —C≡$CR^5$;

$R^5$ is selected from H, $C_1$-$C_6$ alkyl, ethynyl, and $C_3$-$C_7$ cycloalkyl, wherein said $C_1$-$C_6$ alkyl group, said ethynyl group and said $C_3$-$C_7$ cycloalkyl group can be optionally substituted with one or more $R^6$ groups;

each occurrence of $R^6$ is independently selected from $C_1$-$C_6$ alkyl, halo, —$OR^{12}$, $N(R^{12})_2$, —CN, $C_3$-$C_7$ cycloalkyl, phenyl and benzyl;

$R^7$ is H, $C_6$-$C_{10}$ aryl, 5- or 6-membered monocyclic heteroaryl, 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with halo, $C_1$-$C_6$ alkyl, —O—($C_1$-$C_6$ alkyl) or —($C_1$-$C_3$ alkylene)-C(O)O—($C_1$-$C_6$ alkyl);

$R^8$ is H, $C_1$-$C_6$ alkyl, $C_3$-$C_7$ cycloalkyl, phenyl or benzyl;

$R^9$ is H, $C_1$-$C_6$ alkyl, $C_3$-$C_7$ cycloalkyl, phenyl or benzyl;

$R^{10}$ is H, $C_1$-$C_{20}$ alkyl, $C_2$-$C_{20}$ alkenyl, —($C_1$-$C_3$ alkylene)$_m$-($C_3$-$C_7$ cycloalkyl) or —($C_1$-$C_3$ alkylene)$_m$-($C_6$-$C_{10}$ aryl);

$R^{11}$ is H, $C_1$-$C_6$ alkyl, $C_3$-$C_7$ cycloalkyl, —($C_1$-$C_3$ alkylene)$_m$-$C_6$-$C_{10}$ aryl, 5- or 6-membered monocyclic heteroaryl, 9- or 10-membered bicyclic heteroaryl;

each occurrence of $R^{12}$ is independently H, $C_1$-$C_6$ alkyl, $C_3$-$C_7$ cycloalkyl or $C_6$-$C_{10}$ aryl; and each occurrence of m is independently 0 or 1, such that when $R^3$ is —C≡$CR^5$ and $R^4$ is —$OR^{12}$, then $R^1$ and $R^2$ join to form a group having the formula:

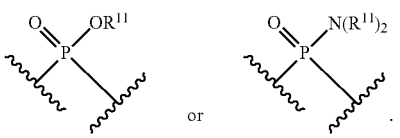

2. The compound of claim 1, wherein X is O.
3. The compound of claim 1, wherein B is uridine.
4. The compound of claim 1, wherein $R^3$ is —C≡$CR^5$.
5. The compound of claim 1, wherein $R^4$ is —C≡$CR^5$.

6. The compound of claim 1 having the formula:

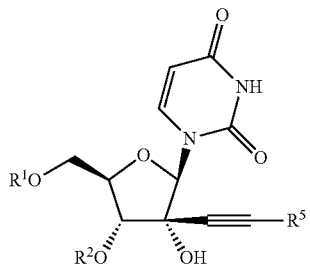
(Ia)

or a pharmaceutically acceptable salt thereof,
wherein:
  $R^1$ and $R^2$ join to form a group having the formula:

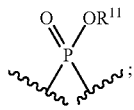;

$R^5$ is H or $C_3$-$C_7$ cycloalkyl; and
  $R^{11}$ is $C_1$-$C_6$ alkyl.

7. The compound of claim 1, wherein $R^1$ is:

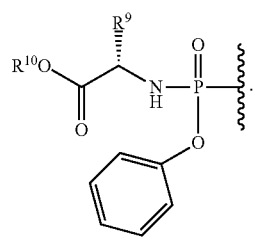

8. The compound of claim 7, wherein $R^1$ is:

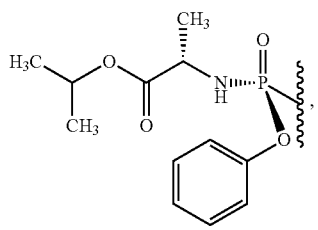

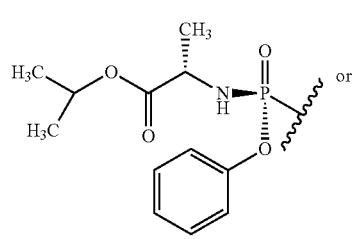 or

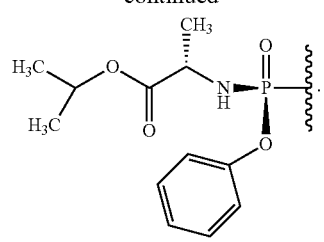

9. The compound of claim 1, wherein $R^1$ and $R^2$ join to form a group having the formula:

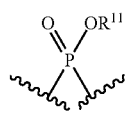

and $R^{11}$ is $C_1$-$C_6$ alkyl.

10. The compound of claim 9, wherein $R^1$ and $R^2$ join to form a group having the structure:

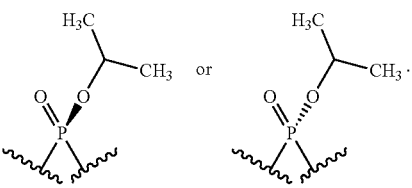

11. A compound having the structure:

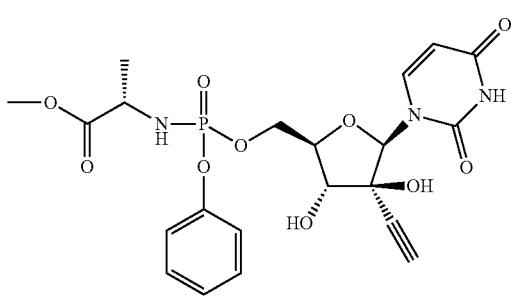

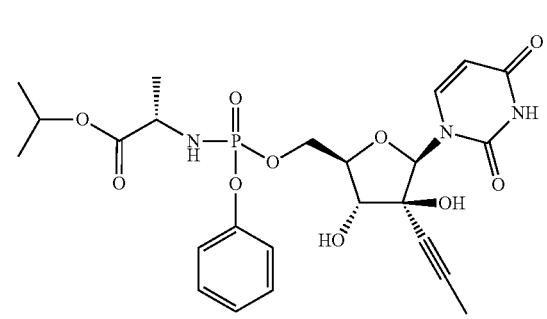

87
-continued
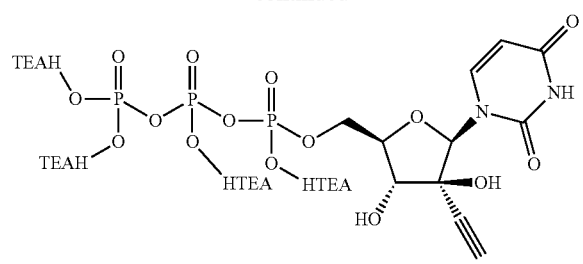
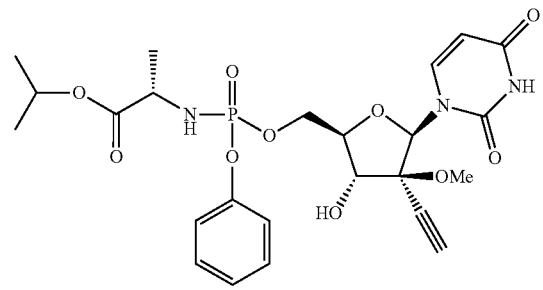
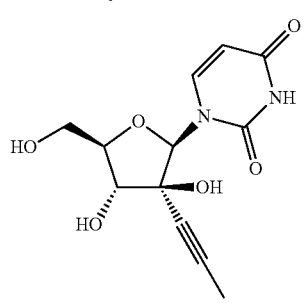
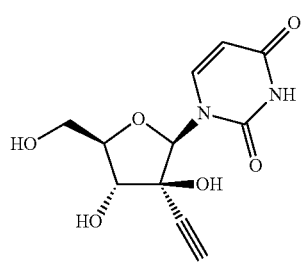
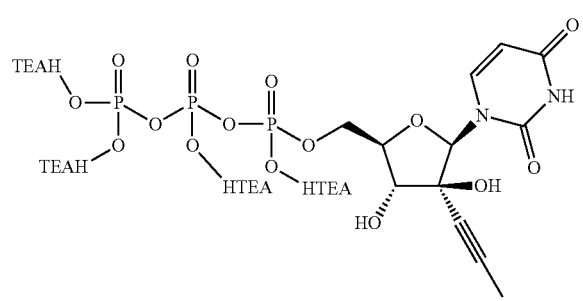
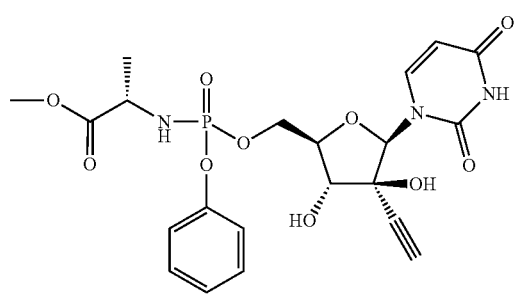
88
-continued
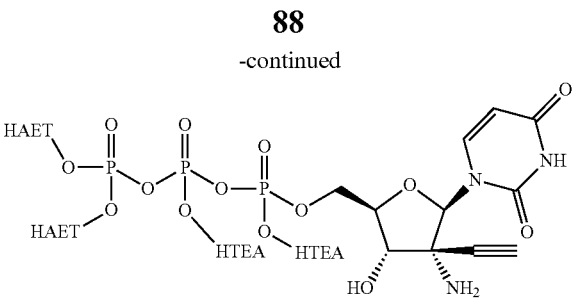
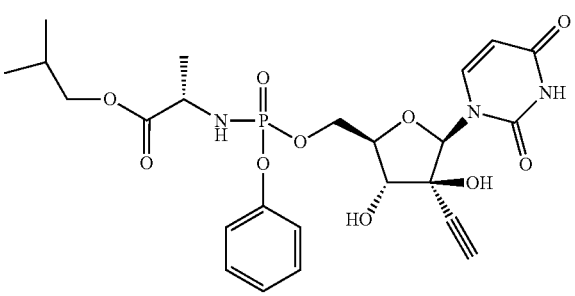
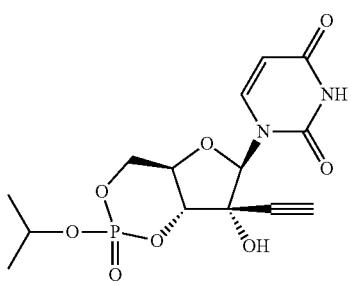
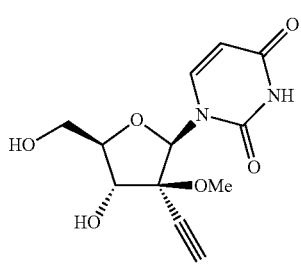
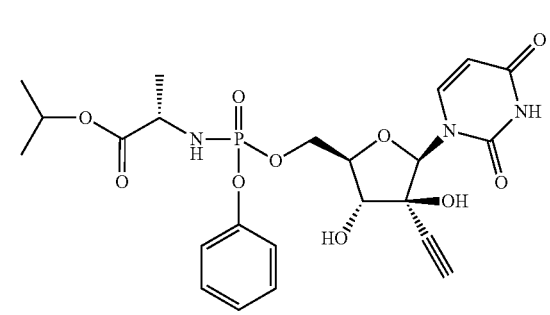
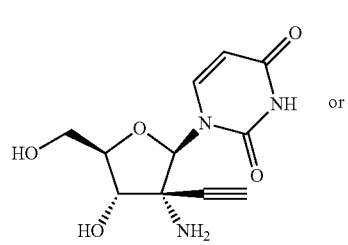
or -continued

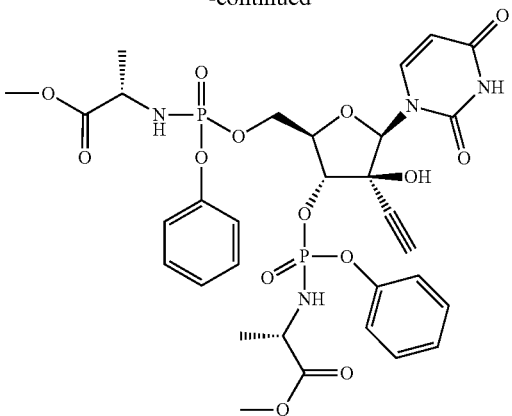

or a pharmaceutically acceptable salt thereof.

12. A pharmaceutical composition comprising an effective amount of the compound of claim 1, or a pharmaceutically acceptable salt thereof, and a pharmaceutically acceptable carrier.

13. The pharmaceutical composition according to claim 12, further comprising a second therapeutic agent selected from the group consisting of HCV antiviral agents, immunomodulators, and anti-infective agents.

14. The pharmaceutical composition according to claim 13, further comprising a third therapeutic agent selected from the group consisting of HCV protease inhibitors, HCV NS5A inhibitors and HCV NS5B polymerase inhibitors.

15. A method of treating a patient infected with HCV comprising the step of administering an amount of the compound of claim 1, or a pharmaceutically acceptable salt thereof, effective to treat infection by HCV in said patient.

16. The method according to claim 15, further comprising the step of administering to said patient a second therapeutic agent selected from the group consisting of HCV antiviral agents, immunomodulators, and anti-infective agents.

17. The method according to claim 16 further comprising the step of further comprising the step of administering to said patient a third therapeutic agent selected from the group consisting of HCV protease inhibitors, HCV NS5A inhibitors and HCV NS5B polymerase inhibitors.

\* \* \* \* \*